United States Patent
King et al.

(10) Patent No.: US 7,977,362 B2
(45) Date of Patent: Jul. 12, 2011

(54) ALPHA-(N-BENZENESULFONAMIDO) CYCLOALKYL DERIVATIVES

(75) Inventors: Dalton King, Hamden, CT (US); Zhaoxing Meng, Middletown, CT (US); Ivar M. McDonald, East Haddam, CT (US); Richard E. Olson, Orange, CT (US); John E. Macor, Guilford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/725,810

(22) Filed: Mar. 17, 2010

(65) Prior Publication Data
US 2010/0240708 A1 Sep. 23, 2010

Related U.S. Application Data

(60) Provisional application No. 61/161,852, filed on Mar. 20, 2009.

(51) Int. Cl.
*A61K 31/4245* (2006.01)
*A61K 31/421* (2006.01)
*C07D 271/06* (2006.01)
*C07D 263/32* (2006.01)

(52) U.S. Cl. ......... 514/364; 514/374; 548/131; 548/235

(58) Field of Classification Search .................. None
See application file for complete search history.

(56) References Cited

U.S. PATENT DOCUMENTS

| | | | |
|---|---|---|---|
| 5,274,094 A | 12/1993 | Whittaker et al. | |
| 5,516,783 A | 5/1996 | Whittaker et al. | |
| 6,153,612 A | 11/2000 | Ortwine et al. | |
| 6,313,123 B1 | 11/2001 | Levin et al. | |
| 7,300,951 B2 | 11/2007 | Kreft et al. | |
| 7,687,666 B2 | 3/2010 | Chan et al. | |
| 7,786,122 B2 | 8/2010 | Parker et al. | |
| 7,838,550 B2 | 11/2010 | Chan et al. | |

FOREIGN PATENT DOCUMENTS

| | | | |
|---|---|---|---|
| JP | 11-343279 | | 12/1999 |
| WO | WO 98/03166 | | 1/1998 |
| WO | WO 00/44716 | | 8/2000 |
| WO | WO 00/50391 | | 8/2000 |
| WO | WO 03/053912 | | 7/2003 |
| WO | WO 2005/042489 | | 5/2005 |
| WO | WO 2005/095334 | | 10/2005 |
| WO | WO 2006/005486 | * | 1/2006 |
| WO | WO 2006/034480 | | 3/2006 |
| WO | WO 2007/098030 | | 8/2007 |
| WO | WO 2008/112249 | | 9/2008 |
| WO | WO 2009/005688 | | 1/2009 |
| WO | WO 2009/058552 | | 5/2009 |
| WO | WO 2009/137657 | | 11/2009 |
| WO | WO 2010/107435 | | 9/2010 |
| WO | WO 2010/107984 | | 9/2010 |
| WO | WO 2010/107997 | | 9/2010 |
| WO | WO 2010/120662 | | 10/2010 |
| WO | WO 2010/120755 | | 10/2010 |

OTHER PUBLICATIONS

U.S. Appl. No. 12/840,612, filed Jul. 21, 2010, Parker et al.
Chapman, P.F. et al., "Impaired synaptic plasticity and learning in aged amyloid precursor protein transgenic mice", Nature Neuroscience, vol. 2, No. 3, pp. 271-276 (1999).
Clarke, W.J. et al., "Gender Differences in Oral Drug Exposure in the Rat with the Gamma-Secretase Inhibitor BMS-708163", Drug Metab. Rev., Abstract No. 126, vol. 41, pp. 58-59 (2009).
Dahlgren, K.N. et al., "Oligomeric and Fibrillar Species of Amyloid-β Peptides Differentially Affect Neuronal Viability", The Journal of Biological Chemistry, vol. 277, No. 35, pp. 32046-32053 (2002).
Freebern, W.J. et al., "From Phenotyping to Host Resistance Models: A Comprehensive Immunotoxicologic Investigation of a Gamma Secretase Inhibitor in Rats", International Journal of Toxicology, Abstract No. P12, vol. 29, No. 1, pp. 91-92 (2010).
Gillman, K.W. et al., "Discovery and Evaluation of BMS-708163, a Potent, Selective and Orally Bioavailable γ-Secretase Inhibitor", ACS Medicinal Chemistry Letters, vol. 1, pp. 120-124 (2010).
Golde, T.E., "Alzheimer's disease therapy: Can the amyloid cascade be halted?", The Journal of Clinical Investigation, vol. 111, No. 1, pp. 11-18 (2003).
Götz, J. et al., "Formation of Neurofibrillary Tangles in P301L Tau Transgenic Mice Induced by Aβ42 Fibrils", Science, vol. 293, pp. 1491-1495 (2001).
Leil, T.A. et al. "Model-Based Trial Simulation for Optimal Collection of CSF Aβ Samples in Clinical Studies: Application for BMS-708163", Clin. Pharmacol. Ther., Abstract No. OII-B-2, vol. 87, Suppl. 1, p. S38 (2010).
Lewis, J. et al., "Enhanced Neurofibrillary Degeneration in Transgenic Mice Expressing Mutant Tau and APP", Science, vol. 293, pp. 1487-1491 (2001).

(Continued)

*Primary Examiner* — Rebecca L Anderson
*Assistant Examiner* — Alicia L Otton
(74) *Attorney, Agent, or Firm* — John F. Levis; Pamela A. Mingo

(57) ABSTRACT

Disclosed are compounds, pharmaceutical compositions containing the compounds, methods for using the compounds and processes for making the compounds. More specifically, the disclosure relates to alpha-(N-benzenesulfonamido)cycloalkyl compounds that may inhibit one or both of: (i) the functioning of a γ-secretase enzyme; or (ii) the production of β-amyloid. Such compounds may be beneficial in the treatment of Alzheimer's disease and other conditions. Representative compounds have the following formula I:

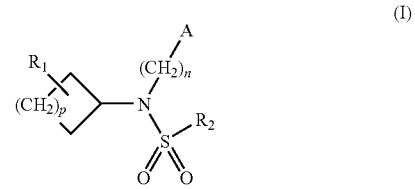

wherein: A, $R_1$, and $R_2$ are described herein.

31 Claims, No Drawings

OTHER PUBLICATIONS

Loane, D.J. et al., "Amyloid precursor protein secretases as therapeutic targets for traumatic brain injury", Nature Medicine, Advance Online Publication, pp. 1-3 (Mar. 15, 2009).

Maharvi, G.M. et al., "A synthesis of the γ-secretase inhibitor BMS-708163", Tetrahedron Letters, online Oct. 14, 2010.

Mayer, S.C. et al., Discovery of Begacestat, a Notch-1-Sparing γ-Secretase Inhibitor for the Treatment of Alzheimer's Disease, Journal of Medicinal Chemistry, vol. 51, No. 23, pp. 7348-7351 (2008).

McLean, C.A. et al., "Soluble Pool of Aβ Amyloid as a Determinant of Severity of Neurodegeneration in Alzheimer's Disease", Annals of Neurology, vol. 46, No. 6, pp. 860-866 (1999).

Seiffert, D. et al., "Presenilin-1 and -2 are Molecular Targets for γ-Secretase Inhibitors", The Journal of Biological Chemistry, vol. 275, No. 44, pp. 34086-34091 (2000).

Selkoe, D.J., "Alzheimer's Disease: Genes, Proteins, and Therapy", Physiological Reviews, vol. 81, No. 2, pp. 741-766 (2001).

Selkoe, D.J., "Cell Biology of the Amyloid β-Protein Precursor and the Mechanism of Alzheimer's Disease", Annu. Rev. Cell Biol., vol. 10, pp. 373-403 (1994).

Siemers, E.R. et al., "Effects of a γ-secretase inhibitor in a randomized study of patients with Alzheimer disease", Neurology, vol. 66, pp. 602-604 (2006).

Thal, D.R. et al., "Two Types of Sporadic Cerebral Amyloid Angiopathy", Journal of Neuropathology and Experimental Neurology, vol. 61, No. 3, pp. 282-293 (2002).

Walsh, D.M. et al., "Naturally secreted oligomers of amyloid β protein potently inhibit hippocampal long-term potentiation in vivo", Nature, vol. 416, pp. 535-539 (2002).

Watkins, T.A. et al., "Distinct Stages of Myelination Regulated by γ-Secretase and Astrocytes in a Rapidly Myelinating CNS Coculture System", Neuron, vol. 60, pp. 555-569 (2008).

Wolfe, M.S., "Secretase Targets for Alzheimer's Disease: Identification and Therapeutic Potential", Journal of Medicinal Chemistry, vol. 44, No. 13, pp. 2039-2060 (2001).

Zhang D. et al., "Disposition of a Gamma-Secretase Inhibitor 14C-Labeled BMS-708163 in Mice, Rats, Rabbits, Dogs, and Humans. Applications of Bile Collection in Differentiating Oxidative Versus Reductive Metabolic Pathways", Drug Metab. Rev., Abstract No. 127, vol. 41, pp. 59-60 (2009).

2008 CSHL Meeting on Neurodegenerative Diseases, Oral Presentation: "BMS-708163, A Potent and Selective Gamma-Secretase Inhibitor, Decreases CSF A-Beta at Safe and Tolerable Doses in Animals and Humans", Dec. 5, 2008.

2009 BMS URG Symposium, Oral Presentation: "The Discovery of BMS-708163: A Potent and Selective Gamma-Secretase Inhibitor for the Treatment of Alzheimer's Disease", May 1, 2009.

237th National American Chemical Society Meeting, Salt Lake City, UT, Oral Presentation: "The Discovery of BMS-708163: A Potent and Selective Gamma-Secretase Inhibitor Which Lowers CSF Beta-Amyloid in Humans", Mar. 22, 2009.

Alzheimer's Association International Conference on Alzheimer's Disease, Chicago, IL, Abstract, Jul. 26, 2008.

Alzheimer's Association International Conference on Alzheimer's Disease, Chicago, IL, Oral Presentation: "BMS-708163, A Potent and Selective Gamma-Secretase Inhibitor, Decreases CSF A-Beta at Safe and Tolerable Doses in Animals and Humans", Jul. 30, 2008.

Alzheimer's Association International Conference on Alzheimer's Disease, Honolulu, HI, Poster: "A Comprehensive Immunotoxicologic Investigation of a Gamma Secretase Inhibitor in Rats", Jul. 10-15, 2010.

Alzheimer's Association International Conference on Alzheimer's Disease, Honolulu, HI, Poster: "A Placebo-Controlled Ascending Multiple-Dose Study to Evaluate the Safety, Pharmacokinetics, and Pharmacodynamics of BMS-708163 in Healthy Young and Elderly Subjects", Jul. 10-15, 2010.

Alzheimer's Association International Conference on Alzheimer's Disease, Honolulu, HI, Poster: "A Study to Evaluate the Effects of Single Oral Doses of BMS-708163 on the Cerebrospinal Fluid A-Beta Level in Healthy Young Men", Jul. 10-15, 2010.

Alzheimer's Association International Conference on Alzheimer's Disease, Honolulu, HI, Poster: "Effect of Concomitant Administration of Multiple Doses of BMS-708163 on Safety and Tolerability and the Pharmacokinetics of Midazolam, Warfarin, Caffeine, Omeprazole, and Dextromethorphan in Healthy Male Subjects by Administration of a Modified Cooperstown Cocktail", Jul. 10-15, 2010.

Alzheimer's Association International Conference on Alzheimer's Disease, Honolulu, HI, Poster: "Gamma-Secretase Inhibitors Have Intrinsically Different Inhibitory Potencies Against A-Beta Production and Notch Signaling", Jul. 10-15, 2010.

Alzheimer's Association International Conference on Alzheimer's Disease, Honolulu, HI, Poster: "Separation of A-Beta Reduction from Notch Toxicity with Gamma-Secretase Inhibitors in Rats", Jul. 10-15, 2010.

Alzheimer's Association International Conference on Alzheimer's Disease, Honolulu, HI, Poster: "The Safety, Tolerability, Pharmacokinetics, and Pharmacodynamics of Single and Multiple Doses of BMS-708163 in Young and Elderly Japanese Subjects", Jul. 10-15, 2010.

Alzheimer's Association International Conference on Alzheimer's Disease, Honolulu, HI, Poster: "The Safety, Tolerability, Pharmacokinetics, and Pharmacodynamics of Single Doses of BMS-708163 in Young and Elderly Subjects", Jul. 10-15, 2010.

American Association of Pharmaceutical Sciences, New Orleans, LA, Oral Presentation: "Simple Allometric Scaling Predicts the Human Dose of BMS-708163, a Gamma Secretase Inhibitor Intended for the Treatment of Alzheimer's Disease", Nov. 14-18, 2010.

AMRI 2010 Integrated Drug Discovery Symposium, Oral Presentation: "Selection and Optimization of a Series of Gamma-Secretase Inhibitors: The Discovery of BMS-708163", Oct. 12-14, 2010.

Bristol-Myers Squibb Symposium, University of California, Irvine, CA, Oral Presentation: "Testing the Amyloid Hypothesis: The Discovery of Brain Penetrant Gamma-Secretase Inhibitors for the Treatment of Alzheimer's Disease", Jun. 2, 2010.

Gordon Research Conference, Newport, RI, Oral Presentation: "Heterocyclic Gamma-Secretase Inhibitors for the Treatment of Alzheimer's Disease", Jun. 30, 2009.

International Society for the Study of Xenobiotics Meeting, Baltimore, MD, Poster: "Gender Differences in Oral Drug Exposure of the Gamma Secretase Inhibitor, BMS-708163, in the Rat", Oct. 18-22, 2009.

Presentation to Department of Chemistry at the University of Arkansas, Fayetteville, AK, Oral Presentation: "Neuroscience Drug Discovery at Bristol-Myers Squibb", Apr. 15, 2010.

* cited by examiner

ALPHA-(N-BENZENESULFONAMIDO) CYCLOALKYL DERIVATIVES

CROSS-REFERENCE TO RELATED APPLICATIONS

This application claims the benefit of U.S. Provisional Application Ser. No. 61/161,852 filed Mar. 20, 2009.

FIELD OF THE INVENTION

This invention generally relates to compounds, pharmaceutical compositions containing the compounds, methods for using the compounds and processes for making the compounds. More specifically, the invention relates to alpha-(N-benzenesulfonamido)cycloalkyl compounds that may be effective in the treatment of Alzheimer's disease and other conditions.

BACKGROUND OF THE INVENTION

Alzheimer's disease (AD) is a progressive neurodegenerative disease which begins with memory loss and progresses to include severe cognitive impairment, altered behavior, and decreased motor function (Grundman, M. et al., *Arch. Neural.*, 61:59-66 (2004); Walsh, D. M. et al., *Neuron*, 44:181-193 (2004)). It is the most common form of dementia and represents the third leading cause of death after cardiovascular disorders and cancer. The cost of AD is enormous and includes the suffering of the patients and families and the lost productivity of patients and caregivers. No treatment that effectively prevents AD or reverses the clinical symptoms and underlying pathophysiology is currently available.

A definitive diagnosis of AD for a demented patient requires a histopathological evaluation of the number and localization of neuritic plaques and neurofibrillary tangles upon autopsy (Consensus recommendations for the postmortem diagnosis of Alzheimer's disease. *Neurobiol. Aging*, 18:S1-S2 (1997)). Similar alterations are observed in patients with Trisomy 21 (Down syndrome). Plaques primarily consist of β-amyloid (Aβ) peptides that are formed by a stepwise proteolytic cleavage of the amyloid precursor protein (APP) by β-site APP-cleaving enzyme (BACE), to generate the N-terminus, and γ-secretase, to generate the C-terminus (Selkoe, D. J., *Physiol. Rev.*, 81:741-766 (2001)). γ-Secretase is a transmembrane protein complex that includes Nicastrin, APH-1, PEN-2, and either Presenilin-1 (PS-1) or Presenilin-2 (PS-2) (Wolfe, M. S. et al., *Science*, 305:1119-1123 (2004)). PS-1 and PS-2 are believed to contain the catalytic sites of γ-secretase.

Aβ40 is the most abundant form of Aβ synthesized (80-90%), while Aβ42 is most closely linked with AD pathogenesis. In particular, mutations in the APP, PS-1, and PS-2 genes that lead to rare, familial forms of AD implicate Aβ42 aggregates as the primary toxic species (Selkoe, D. J., *Physiol, Rev.*, 81:741-766 (2001)). Current evidence suggests that oligomeric, protofibrillar and intracellular Aβ42 play a significant role in the disease process (Cleary, J. P. et al., *Nat. Neurosci.*, 8:79-84 (2005)). Inhibitors of the enzymes that form Aβ42, such as γ-secretase, represent potential disease-modifying therapeutics for the treatment of AD.

γ-Secretase cleaves multiple type I transmembrane proteins in addition to APP (Pollack, S. J. et al., *Curr. Opin. Investig, Drugs*, 6:35-47 (2005)). While the physiological significance of most of these cleavage events is unknown, genetic evidence indicates that γ-secretase cleavage of Notch is required for Notch signaling (Artavanis-Tsakonas, S. et al., *Science*, 284(5415):770-776 (1999); Kadesch, T., *Exp. Cell Res.*, 260(1):1-8 (2000)). In rodents dosed with γ-secretase inhibitors, drug-related toxicity has been identified in the gastrointestinal (GI) tract, thymus, and spleen (Searfoss, G. H. et al., *J. Biol. Chem.*, 278:46107-46116 (2003); Wong, G. T. et al., *J. Biol. Chem.*, 279:12876-12882 (2004); Milano, J. et al., *Toxicol. Sci.*, 82:341-358 (2004)). These toxicities are likely linked to inhibition of Notch signaling (Jensen, J. et al., *Nat. Genet.*, 24:36-44 (2000)).

The identification of mechanism-based toxicity raises the question of whether an acceptable therapeutic index can be achieved with γ-secretase inhibitors. Selective inhibition of Aβ formation over Notch processing, pharmacokinetics, drug disposition and/or tissue-specific pharmacodynamics could impact therapeutic margin.

Evidence suggests that a reduction in brain Aβ levels by inhibition of γ-secretase may prevent the onset and progression of AD (Selkoe, D., *Physiol. Rev.*, 81:741-766 (2001); Wolfe, M., *J. Med. Chem.*, 44:2039-2060 (2001)). There are emerging data for the role of Aβ in other diseases, including mild cognitive impairment (MCI), Down syndrome, cerebral amyloid angiopathy (CAA), dementia with Lewy bodies (DLB), amyotrophic lateral sclerosis (ALS-D), inclusion body myositis (IBM), and age-related macular degeneration. Advantageously, compounds that inhibit γ-secretase and reduce production of Aβ could be used to treat these or other Aβ-dependent diseases.

Excess production and/or reduced clearance of Aβ causes CAA (Thal, D. et al., *J. Neuropath. Exp. Neuro.*, 61:282-293 (2002)). In these patients, vascular amyloid deposits cause degeneration of vessel walls and aneurysms that may be responsible for 10-15% of hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients. Compounds that specifically target γ-secretase could reduce or prevent CAA.

DLB manifests with visual hallucinations, delusions, and parkinsonism. Interestingly, familial AD mutations that cause Aβ deposits can also cause Lewy bodies and DLB symptoms (Yokota, O. et al., *Acta Neuropathol. (Berl.)*, 104:637-648 (2002)). Further, sporadic DLB patients have Aβ deposits similar to those in AD (Deramecourt, V. et al., *J. Neuropathol. Exp. Neural.*, 65:278-288 (2006)). Based on this data, Aβ likely drives Lewy body pathology in DLB and, therefore, γ-secretase inhibitors could reduce or prevent DLB.

Approximately 25% of ALS patients have significant dementia or aphasia (Hamilton, R. L. et al., *Acta Neuropathol. (Berl.)*, 107:515-522 (2004)). The majority (~60%) of these patients, designated ALS-D, contain ubiquitin-positive inclusions comprised primarily of the TDP-43 protein (Neumann, M. et al., *Science*, 314:130-133 (2006)). About 30% of the ALS-D patients have amyloid plaques consistent with Aβ causing their dementia (Hamilton, R. L. et al., *Acta Neuropathol. (Berl.)*, 107:515-522 (2004)). These patients should be identifiable with amyloid imaging agents and potentially treatable with γ-secretase inhibitors.

IBM is a rare, age-related degenerative disease of skeletal muscle. The appearance of Aβ deposits in IBM muscle and the recapitulation of several aspects of the disease by directing APP overexpression to muscle in transgenic mice support the role of Aβ in IBM (reviewed in Murphy, M. P. et al., *Neurology*, 66:S65-S68 (2006)). Compounds that specifically target γ-secretase could reduce or prevent IBM.

In age-related macular degeneration, Aβ was identified as one of several components of drusen, extracellular deposits beneath the retinal pigment epithelium (RPE) (Anderson, D. H. et al., *Exp. Eye Res.*, 78:243-256 (2004)). A recent study has shown potential links between Aβ and macular degeneration in mice (Yoshida, T. et al., *J. Clin. Invest.*, 115:2793-2800 (2005)). Increases in Aβ deposition and supranuclear cataracts have been found in AD patients (Goldstein, L. E. et al., *Lancet*, 361:1258-1265 (2003)). Compounds that specifically target γ-secretase could reduce or prevent age-related macular degeneration.

Based on the role of Notch signaling in tumorigenesis, compounds which inhibit γ-secretase may also be useful as therapeutic agents for the treatment of cancer (Ship, I.-M. et al., *Cancer Res.*, 67:1879-1882 (2007)).

Accordingly, new compounds are desired that may inhibit the functioning of the enzymes that form Aβ42, such as γ-secretase. Such compounds may have utility in treating various diseases including, for example, AD, and other conditions associated with β-AP formation.

SUMMARY OF THE INVENTION

In accordance with the present invention, compounds, pharmaceutical compositions containing the compounds, methods for using the compounds and processes for making the compounds are provided. The compounds may be useful for the treatment of diseases, for example, AD, and other conditions associated with β-AP formation. The compounds, which may be described as alpha-(N-benzenesulfonamido) cycloalkyl compounds, may inhibit one or both of: (i) the functioning of a γ-secretase enzyme; or (ii) the production of β-amyloid. The pharmacologic action of these compounds may make them useful for treating conditions responsive to the inhibition of β-AP in a patient; e.g., AD, and useful for treating conditions responsive to the inhibition of a γ-secretase enzyme.

DETAILED DESCRIPTION OF THE INVENTION

The term "$C_{1-3}$ alkyl" as used herein means straight or branched chain alkyl groups such as methyl, ethyl or propyl. Unless otherwise specified, the term "halogen" as used herein is intended to include bromine, chlorine, iodine and fluorine while the term "halide" is intended to include bromide, chloride and iodide anion.

The term "compounds of the present invention", and equivalent expressions, are meant to embrace compounds of Formula I, II, III, and pharmaceutically acceptable salts thereof. Similarly, references to intermediates are meant to embrace their salts where the context so permits.

The term "patient" includes both human and other mammals.

The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

The term "pharmaceutically acceptable salt," as used herein, represents salts or zwitterionic forms of the compounds of the present invention which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, dihydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

The term "therapeutically effective amount" means the total amount of each active component of the method that is sufficient to show a patient benefit, i.e., symptomatic or disease modifying treatment. When applied to an individual active ingredient, administered alone, the term refers to that ingredient alone. When applied to a combination, the term refers to combined amounts of the active ingredients that result in the therapeutic effect, whether administered in combination, serially or simultaneously.

As the compounds of the present invention possess an asymmetric carbon atom, the present invention includes the racemate as well as the individual enantiomeric forms of the compounds of Formula I, II and III as described herein. The use of a single designation such as (R) or (S) is intended to include mostly one stereoisomer. Mixtures of isomers can be separated into individual isomers according to methods which are known per se, e.g., fractional crystallization, adsorption chromatography or other suitable separation processes. Resulting racemates can be separated into antipodes in the usual manner after introduction of suitable salt-forming groupings, e.g., by forming a mixture of diastereoisomeric salts with optically active salt-forming agents, separating the mixture into diastereomeric salts and converting the separated salts into the free compounds. The possible enantiomeric forms may also be separated by fractionation through chiral high pressure liquid chromatography columns. Certain compounds of the present invention may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

All patents, patent applications, and literature references cited in the specification are herein incorporated by reference in their entirety. In the case of inconsistencies, the present disclosure, including definitions, will prevail.

In one aspect of the invention, there is provided a compound of formula I:

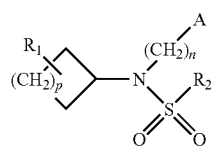

wherein:

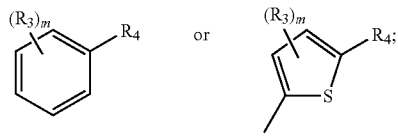

A is
$R_1$ is —$CH_2F$, —$CH_2OH$, —$CH(CH_3)OH$, —$C(CH_3)_2OH$, —$COCH_3$, or $R_1$ is —CHOH wherein the carbon atom of $R_1$ is bonded to two different positions on the cyclic alkyl ring of Compound I;
$R_2$ is selected from the group consisting of phenyl, thiophene and pyridine, each optionally substituted with 1, 2, 3, or 4 substituents selected from the group consisting of hydrogen, halogen and trifluoromethyl;
$R_3$, if present, is halogen;

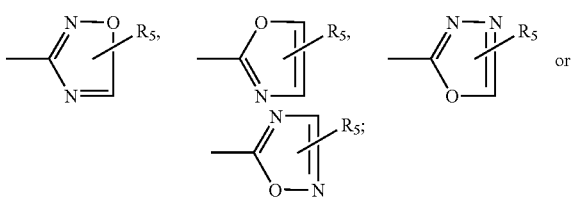

$R_4$ is
$R_5$ is H, $C_{1-3}$alkyl or $CF_3$;
m is 0, 1, 2, 3 or 4;
n is 0, 1, 2, 3, or 4;
p is 0, 1, 2, 3, 4 or 5;
or a pharmaceutically acceptable salt thereof.

A specific aspect of the invention provides a compound of formula I wherein A is:

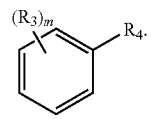

A specific aspect of the invention provides a compound of formula I wherein n is 0. Another specific aspect of the invention provides a compound of formula I wherein n is 1, 2, 3, or 4, preferably 1.

A specific aspect of the invention provides a compound of formula I wherein $R_4$ is

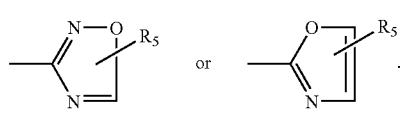

A specific aspect of the invention provides a compound of formula I wherein $R_5$ is H. Another specific aspect of the invention provides a compound of formula I wherein $R_5$ is $C_{1-3}$alkyl or $CF_3$.

A specific aspect of the invention provides a compound of formula I wherein $R_3$ is F, Cl or Br, preferably F.

A specific aspect of the invention provides a compound of formula I wherein m is 0. Another specific aspect of the invention provides a compound of formula I wherein m is 1 or 2.

A specific aspect of the invention provides a compound of formula I wherein $R_2$ is selected from the group consisting of phenyl, thiophene and pyridine, each optionally substituted with one substituent selected from the group consisting of hydrogen, halogen and trifluoromethyl. Another specific aspect of the invention provides a compound of formula I wherein $R_2$ is selected from the group consisting of phenyl, thiophene and pyridine, each optionally substituted with 2, 3, or 4 substituents selected from the group consisting of hydrogen, halogen and trifluoromethyl.

A specific aspect of the invention provides a compound of formula I wherein $R_1$ is —$CH_2F$, —$CH_2OH$, —$CH(CH_3)OH$, —$C(CH_3)_2OH$, or —$COCH_3$, preferably —$CH_2F$, —$CH_2OH$, —$CH(CH_3)OH$, —$C(CH_3)_2OH$, and more preferably —$CH_2OH$.

A specific aspect of the invention provides a compound of formula I wherein p is 2, 3 or 4.

In another aspect of the invention, there is provided a compound of formula II:

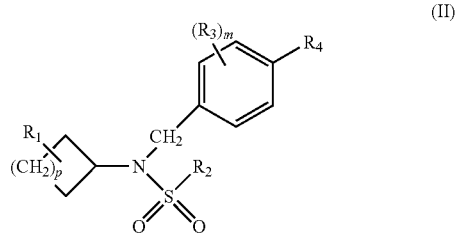

wherein:
$R_1$ is —$CH_2F$, —$CH_2OH$, —$CH(CH_3)OH$, —$C(CH_3)_2OH$, —$COCH_3$, or $R_1$ is —CHOH wherein the carbon atom of $R_1$ is bonded to two different positions on the cyclic alkyl ring of Compound II;

$R_2$ is

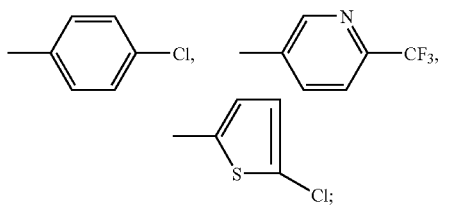

$R_3$, if present, is F;
R4 is

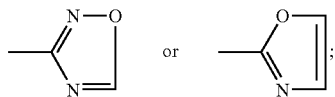

m is 0, 1 or 2;
p is 2, 3 or 4;
or a pharmaceutically acceptable salt thereof.

A specific aspect of the invention provides a compound of formula II wherein $R_2$ is

A specific aspect of the invention provides a compound of formula II wherein $R_1$ is —CH$_2$F, —CH$_2$OH, —CH(CH$_3$)OH, —C(CH$_3$)$_2$OH, or —COCH$_3$, preferably, —CH$_2$OH.

A specific aspect of the invention provides a compound of formula II wherein p is 3.

In another aspect of the invention, there is provided a compound of formula III:

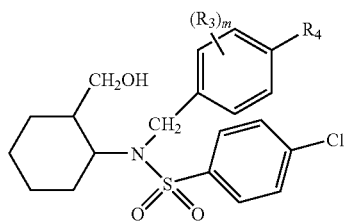

(III)

wherein:
$R_3$, if present, is F;
R4 is

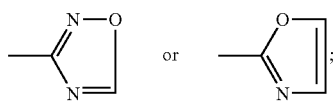

m is 0, 1 or 2;
or a pharmaceutically acceptable salt thereof.

A specific aspect of the invention provides a compound of formula III wherein $R_3$ is F.

A specific aspect of the invention provides a compound of formula III wherein m is 1 or 2.

Another aspect of the invention provides a compound having the following structure, also referred to as 4-chloro-N-(2,3-difluoro-4-(oxazol-2-yl)benzyl)-N-((1R,2R)-2-(hydroxymethyl)cyclohexyl)benzenesulfonamide:

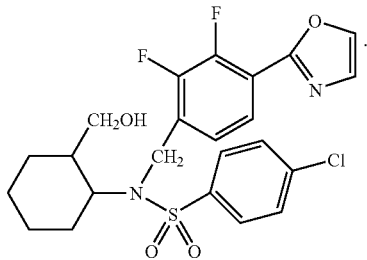

Another aspect of the invention provides a compound having the following structure, also referred to as N-(4-(1,2,4-oxadiazol-3-yl)benzyl)-4-chloro-N-((1R,2R)-2-(hydroxymethyl)cyclohexyl)benzenesulfonamide:

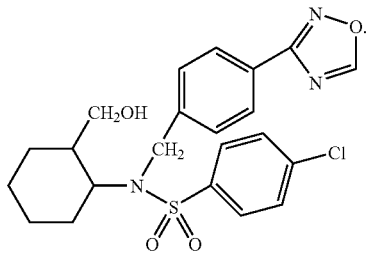

Another aspect of the invention provides a compound having the following structure, also referred to as 4-chloro-N-(2-fluoro-4-(oxazol-2-yl)benzyl)-N-((1R,2R)-2-(hydroxymethyl)cyclohexyl)benzenesulfonamide:

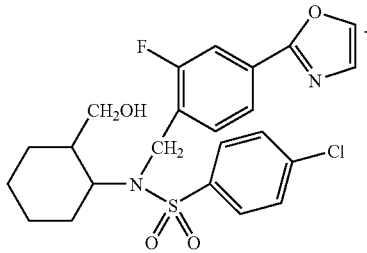

Another aspect of the invention provides a compound having the following structure, also referred to as 4-chloro-N-(2,5-difluoro-4-(1,2,4-oxadiazol-3-yl)benzyl)-N-((1R,2R)-2-(hydroxymethyl)cyclohexyl)benzenesulfonamide:

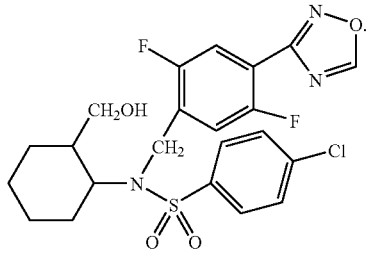

Another aspect of the invention provides a composition comprising a compound of the invention, or a pharmaceutically acceptable salt thereof, and a pharmaceutically acceptable carrier.

Another aspect of the invention provides method of treating or delaying the onset of Alzheimer's disease, cerebral amyloid angiopathy, mild cognitive impairment and/or Down syndrome which comprises administering to a patient a therapeutically effective amount of a compound of the invention, or a pharmaceutically acceptable salt thereof.

Another specific aspect of the invention provides a method of treating Alzheimer's disease in a patient, comprising administering to the patient a therapeutically effective amount of a compound of the invention, or a pharmaceutically acceptable salt thereof.

Another aspect of the invention provides a method of inhibiting the functioning of a γ-secretase enzyme comprising contacting the γ-secretase enzyme with an effective amount of a compound of the invention, or a pharmaceutically acceptable salt thereof. Accordingly, the compounds of the invention may also be useful in treating conditions associated with loss of myelination, for example multiple sclerosis.

Another aspect of the invention provides a method of inhibiting the production of β-amyloid peptide in a patient, comprising contacting a γ-secretase enzyme in the patient with an effective amount of a compound of the invention, or a pharmaceutically acceptable salt thereof.

Another aspect of the invention provides a method of inhibiting the production of β-amyloid peptide in a patient, comprising administering to the patient a therapeutically effective amount of a compound of the invention, or a pharmaceutically acceptable salt thereof. Stated another way, an aspect of the invention provides a method of treatment of disorders responsive to the inhibition of β-amyloid peptide. Examples of such diseases or conditions include Alzheimer's disease, cerebral amyloid angiopathy, systemic amyloidosis, hereditary cerebral hemorrhage with amyloidosis of the Dutch type, multi-infarct dementia, mild cognitive impairment and Down syndrome. Another example of such a condition where inhibition of β-amyloid peptide production may be beneficial is in the treatment of traumatic brain injury. The compounds of the invention may be effective to inhibit the accumulation of Aβ peptides and/or amyloid protein deposits in the brain, and accordingly may be useful in the treatment of head trauma, traumatic brain injury, dementia pugilistica, and/or other conditions associated with β-amyloid peptide.

General Reaction Schemes

General procedures that can be used to synthesize the compounds of the invention are described in following reaction schemes. Those skilled in the art will recognize that other reaction schemes, or variations of the following schemes, may be employed to make the compounds of the invention. The starting materials suitable for use in making the compounds of the invention are readily available commercially or can be synthesized by those skilled in the art. The present invention includes processes for making the compounds of the invention according to the reaction schemes set for the below.

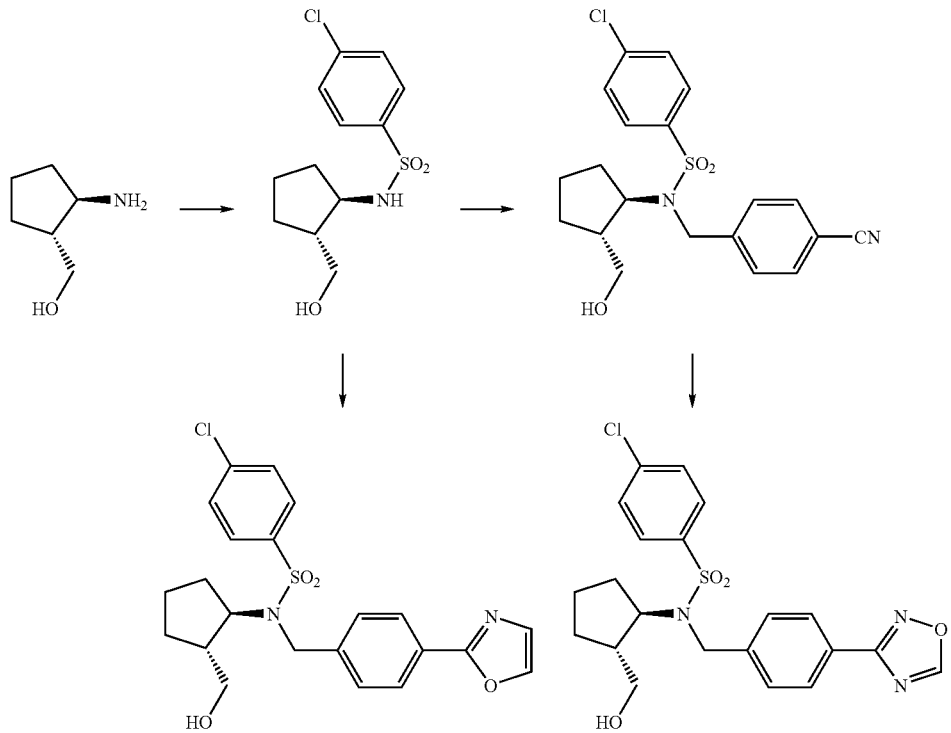

Scheme 1

Scheme 2
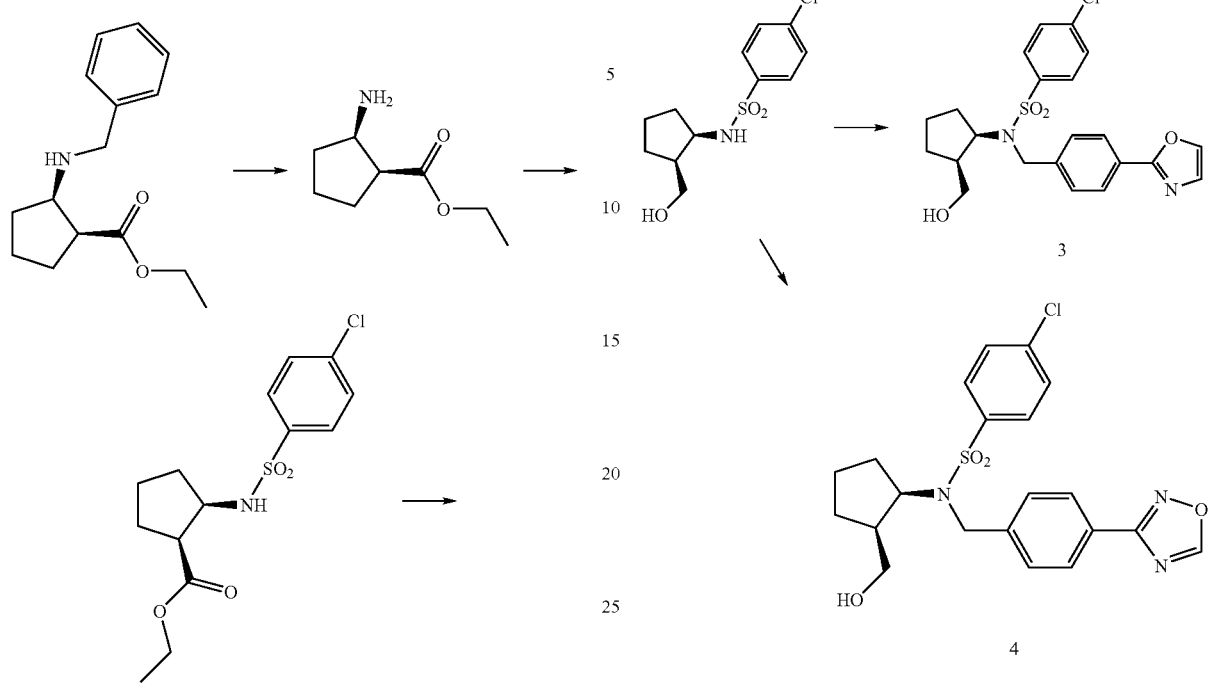
Scheme 3
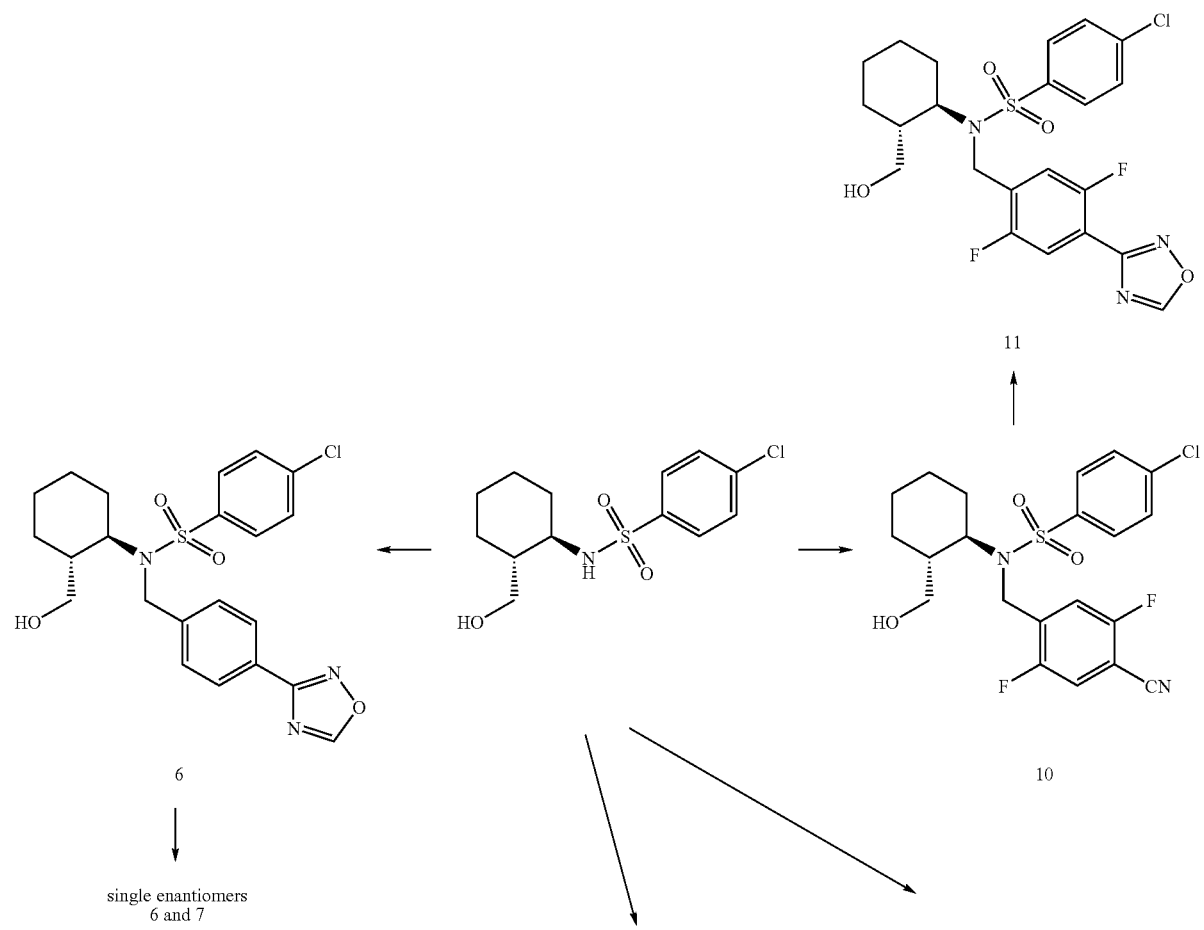
single enantiomers
6 and 7

13                                                                14
-continued
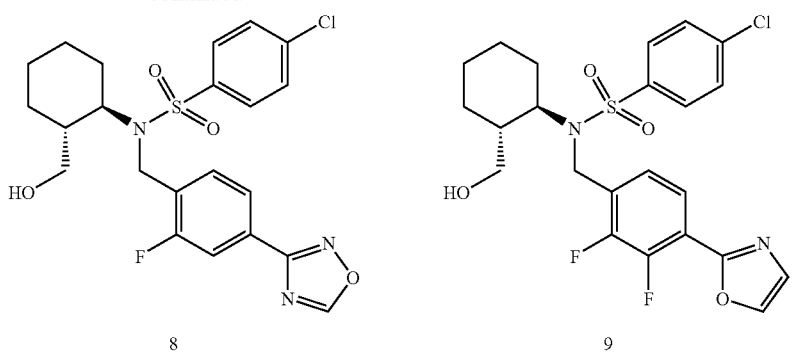
8                                                                 9
Scheme 4
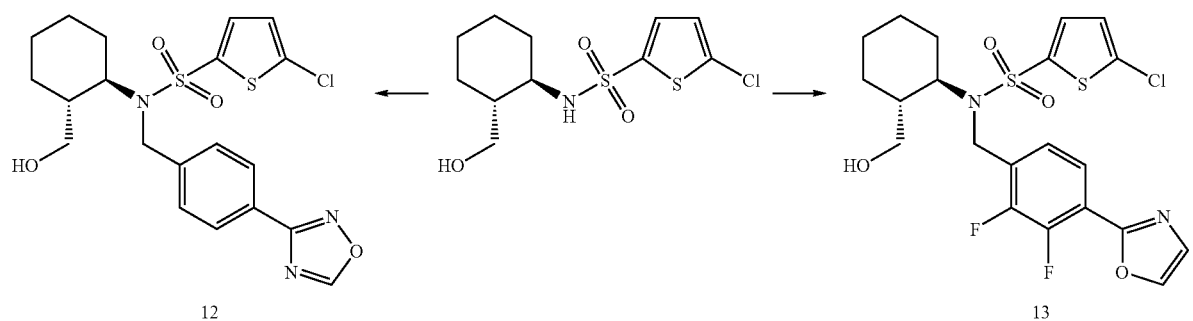
12                                                                13
Scheme 5
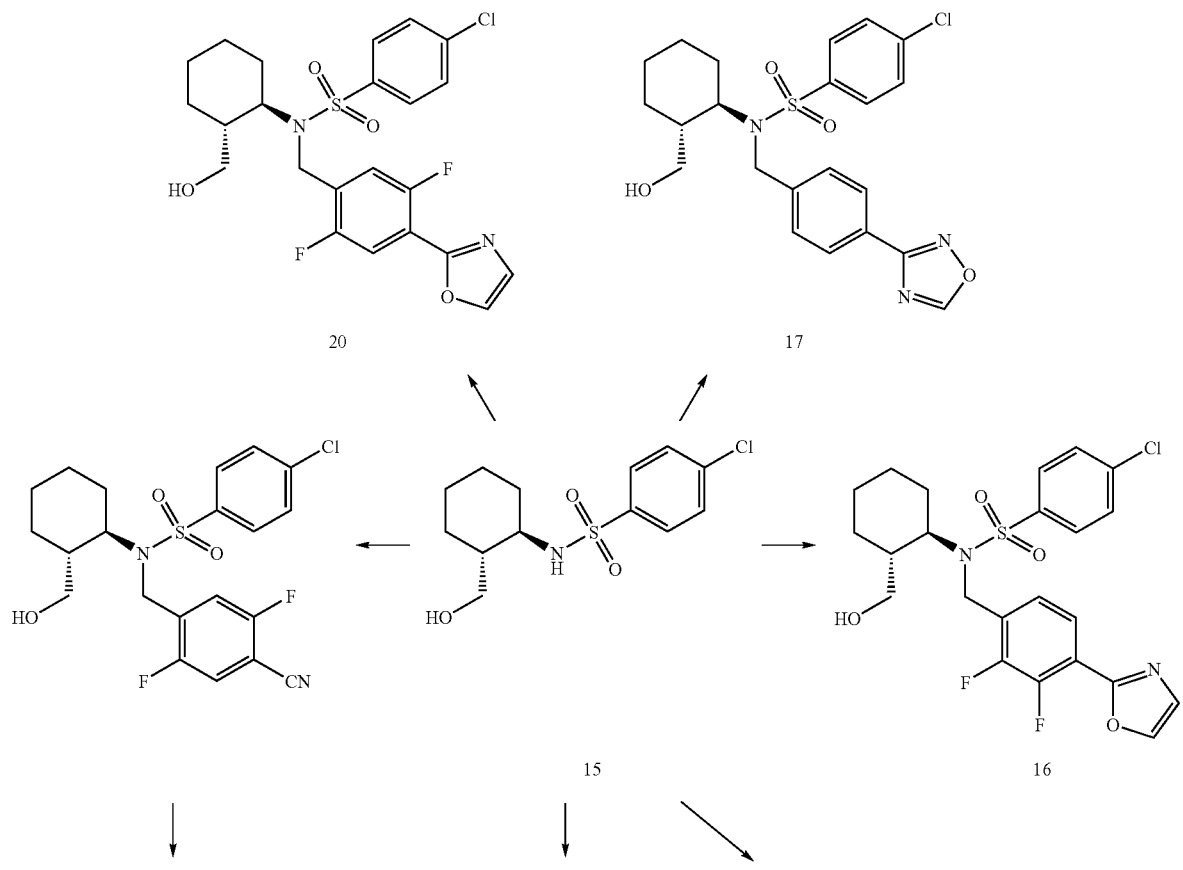
20                                      17
15                                      16

15
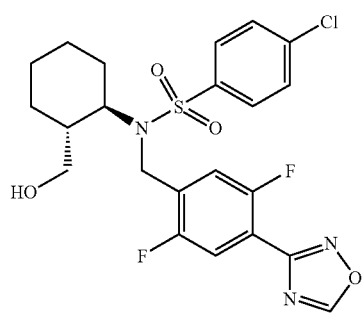
21
-continued
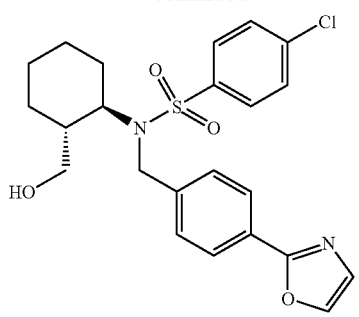
18
16
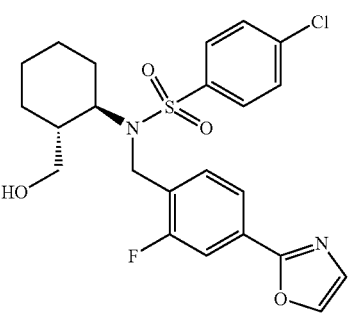
19
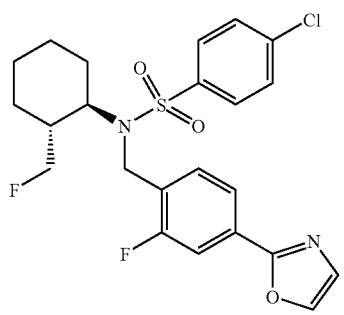
22
Scheme 6
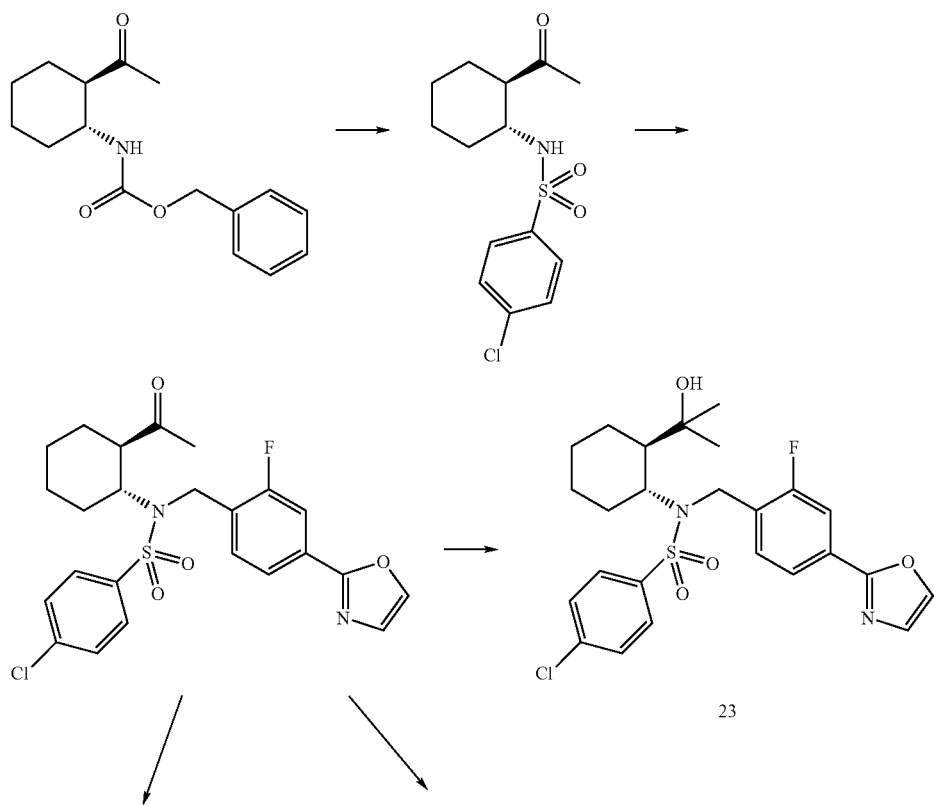
23

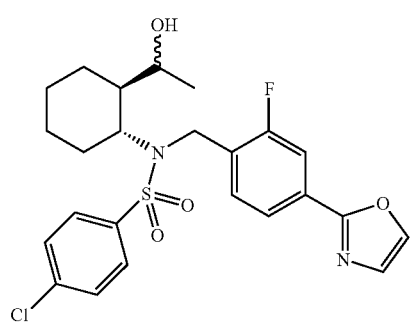
24
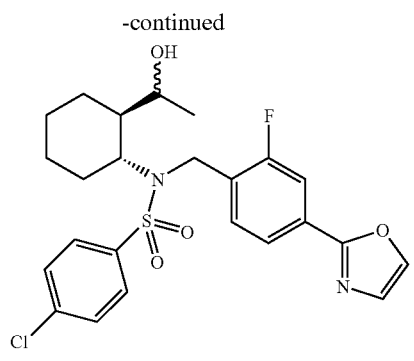
25
Scheme 7
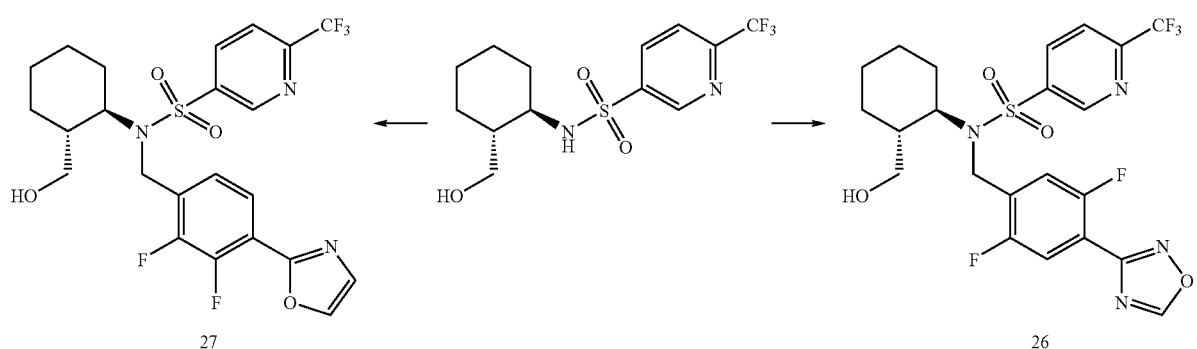
27 26
Scheme 8
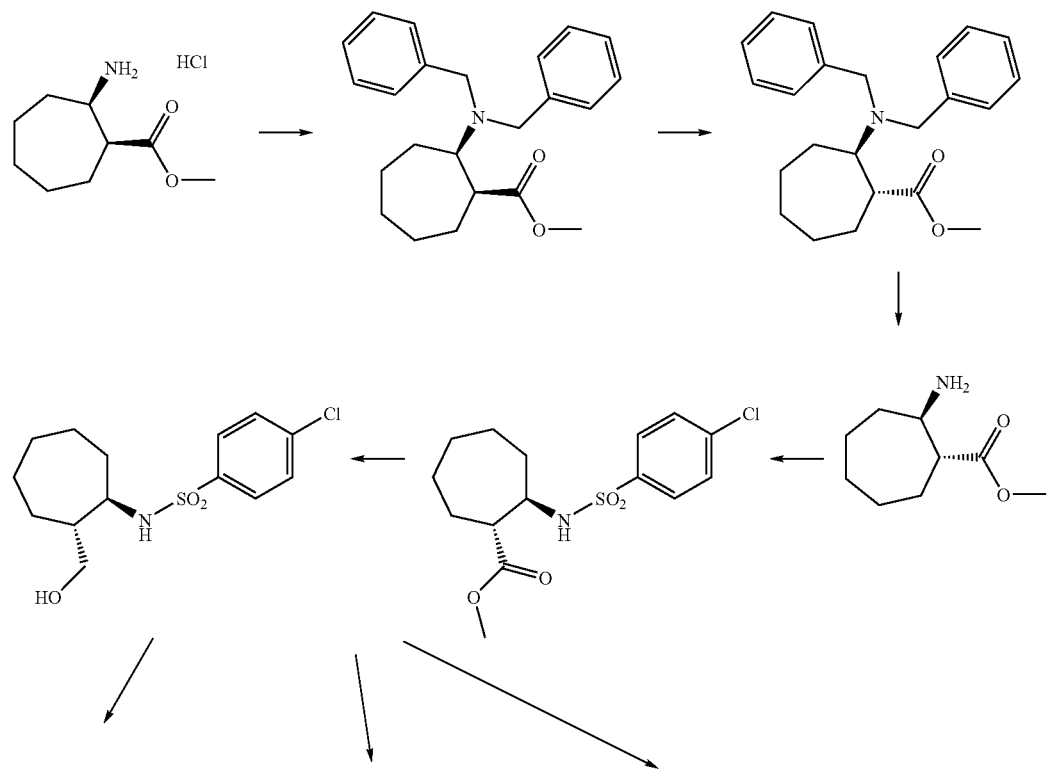

19
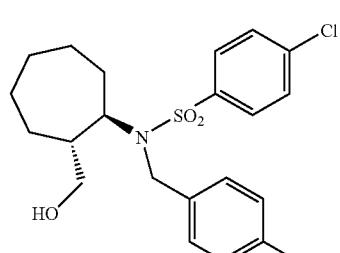
28
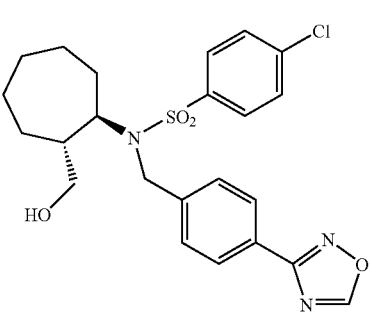
29
20
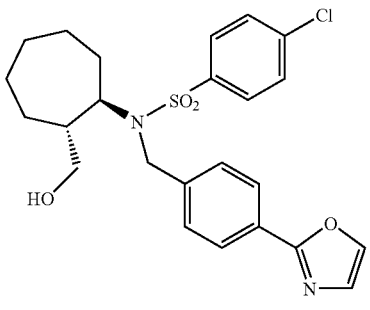
30
-continued
Scheme 9
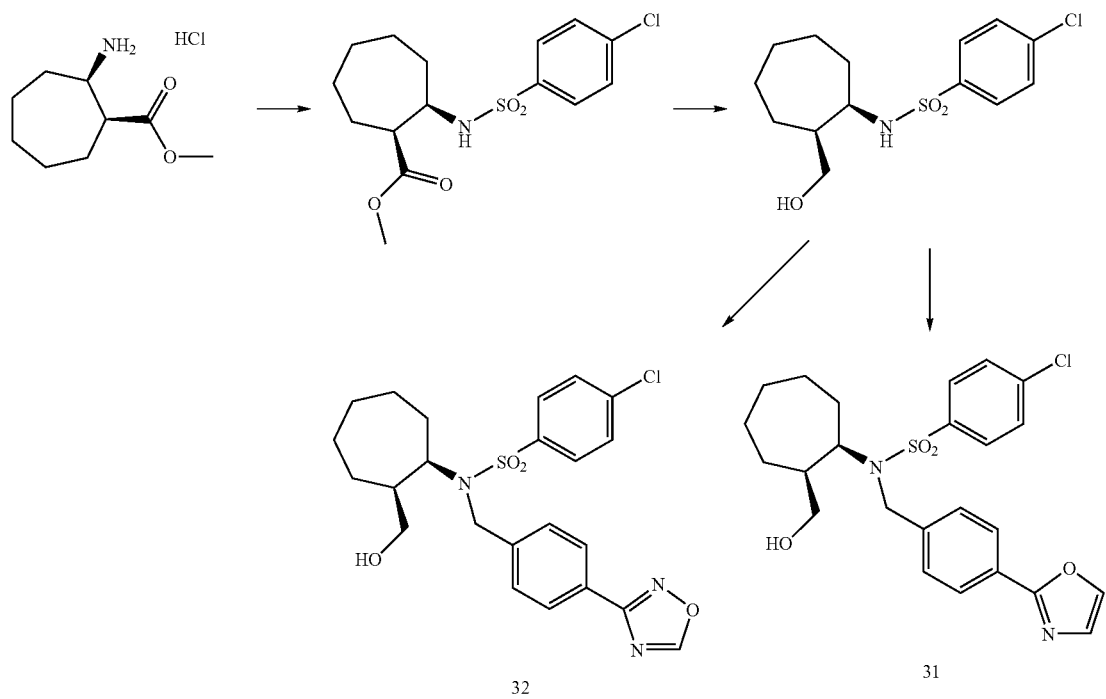
32
31
Scheme 10
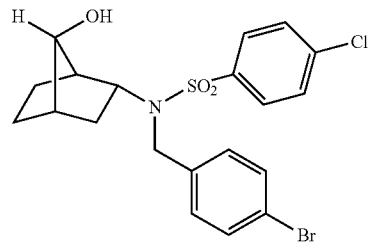
33

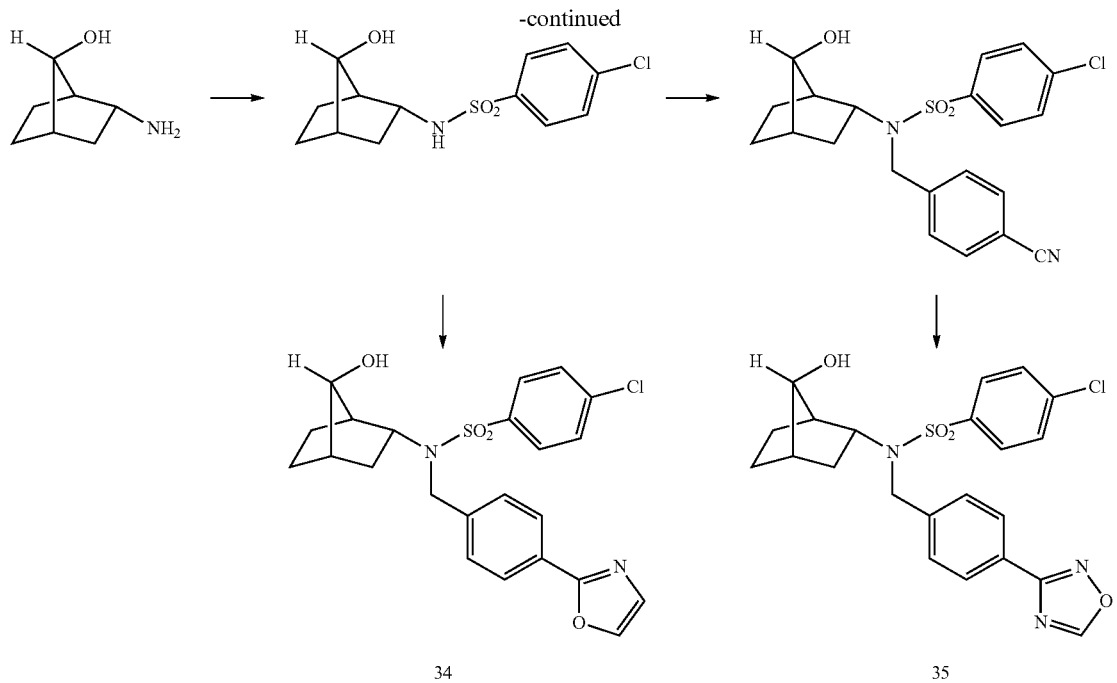

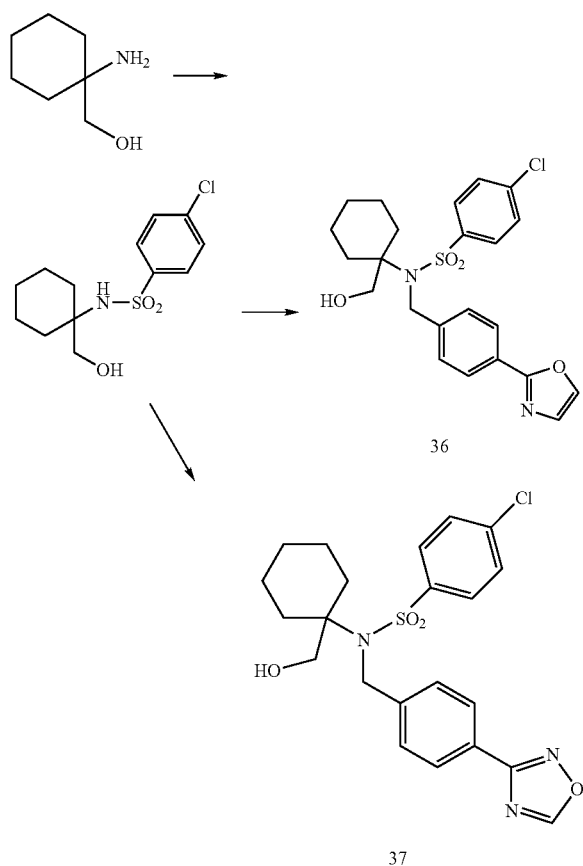

Scheme 11

Typically, for use in therapy, therapeutically effective amounts of a compound of the invention are administered as an active ingredient in a pharmaceutical composition. Accordingly, the invention further provides pharmaceutical compositions, which include therapeutically effective amounts of a compound of the invention or pharmaceutically acceptable salts thereof, and one or more pharmaceutically acceptable carriers.

In accordance with another aspect of the present invention there is also provided a process for the preparation of a pharmaceutical composition including admixing a compound of the invention or a pharmaceutically acceptable salt thereof, with one or more pharmaceutically acceptable carriers.

Pharmaceutical compositions may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such compositions may be prepared by any method known in the art of pharmacy, for example by bringing into association the active ingredient with the carrier(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit compositions for oral administration can be microencapsulated. The formulation can also be prepared to prolong or sustain the release as for example by coating or embedding particulate material in polymers, wax, or the like.

Further details concerning the manufacture of pharmaceutical compositions are known to those skilled in the art. See, for example, *Remington's Pharmaceutical Sciences*, Mack Publishing Company, Easton, Pa., 17th edition (1985).

Pharmaceutical compositions of the present invention may be presented in unit dose forms containing a predetermined amount of active ingredient per unit dose. Generally, dosage levels may be between about 0.01 and about 250 milligram per kilogram ("mg/kg") body weight per day, preferably between about 0.05 and about 100 mg/kg body weight per day of the compounds of the present invention. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects. The decision as to the particular dosage to be employed (and the number of times to be administered per day) is within the discretion of the physician, and may be varied by titration of the dosage to the particular circumstances of this invention to produce the desired therapeutic effect.

As an example, the dose of a compound of the invention for a patient suffering from, or likely to suffer from, a condition related to Aβ peptide production as described herein, generally the daily dose will be from about 0.01 mg/kg to about 10 mg/kg and often, about 0.1 to 2 mg/kg when administered parenterally. For oral administration, the dose may be in the range from about 0.01 to about 20 mg/kg and often from 0.1 to 10 mg/kg body weight. The active ingredient will typically be administered in equal doses from one to four times a day. However, usually a small dosage is administered, and the dosage is gradually increased until the optimal dosage for the patient under treatment is determined. In accordance with good clinical practice, it is preferred to administer the instant compound at a concentration level that will produce an effective anti-amyloid effect without causing any harmful or untoward side effects. However, it will be understood that the amount of the compound actually administered will be determined by a physician, in the light of the relevant circumstances.

When the compositions of this invention comprise a combination of a compound of the present invention and one or more additional therapeutic or prophylactic agent, both the compound and the additional agent are usually present at dosage levels of between about 10 to 150%, and more preferably between about 10 and 80% of the dosage normally administered in a monotherapy regimen.

Accordingly, the pharmaceutical compositions of the present invention include those that also contain one or more other active ingredients, in addition to a compound of the invention. Examples of other active ingredients that may be combined with a compound of the invention, either administered separately or in the same pharmaceutical compositions, to treat diseases or conditions, e.g., Alzheimer's disease, include but are not limited to: the class of drugs which are cholinesterase inhibitors, for example donepezil (ARICEPT®), rivastigmine (EXELON®), galantamine (REMINYL®, now RAZADYNE®); other drugs which are NMDA antagonists such as memantine (NAMENDA®) and PDE4 inhibitors such as cilomilast (ARIFLO®); the class of NSAIDs, such as R-flurbiprofen (FLURIZAN®); the cholesterol-lowering statin drugs such as pravastatin, simvastatin, and atorvastatin; anti-amyloid and anti-Aβ immune therapy; compounds which inhibit the aggregation of Aβ such as scyl-loinositol and clioquinol; other compounds which inhibit or modify Aβ production or processing such as γ-secretase inhibitors, β-secretase inhibitors, γ-secretase modulators, Aβ modulators, and GSK-3 inhibitors; compounds which regulate Aβ turnover such as PAI-1 inhibitors; compounds which regulate tau phosphorylation such as GSK-3 and CDK-5 inhibitors; PPARγ agonists such as rosiglitazone; compounds which regulate tau or phosphor-tau turnover, or oligomerization such as HSP90 inhibitors, HDAC inhibitors and anti-tau immune therapy; and compounds which stabilize or bind to microtubules, such as taxane derivatives and epothilone derivatives; and compounds which regulate mitochondria function such as Dimebon.

The compounds of the present invention may be used with known anti-cancer agents or treatments. Such agents and treatments include cytotoxic/cytostatic agents, androgen receptor modulators, estrogen receptor modulators, retinoid receptor modulators, prenyl-protein transferase inhibitors, angiogenesis inhibitors, agents that interfere with cell-cycle checkpoints, and radiation therapy. In addition, the compounds of the present invention may be useful in the treatment of immunological disorders such as Lupus.

The above therapeutic agents, when employed in combination with the compound of the present invention, may be used, for example, in those amounts indicated in the Physicians' Desk Reference (PDR), where applicable or as otherwise determined by one of ordinary skill in the art.

The following examples are given by way of illustration and are not to be construed as limiting the invention.

EXAMPLES

In the following examples, all temperatures are given in degrees Centigrade. Proton magnetic resonance ($^1$H NMR) spectra were recorded on a Bruker Avance 300, a Bruker Avance 400, or a Bruker Avance 500 spectrometer. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; ddd, doublet a doublet of doublet; br d, broad doublet; dt, doublet of triplet; br s, broad singlet; dq, doublet of quartet. Optical rotations [α]$_D$ were determined on a Rudolph Scientific Autopol IV polarimeter in the solvents indicated; concentrations are given in mg/mL. Low resolution mass spectra (MS) and the apparent molecular (MH$^+$) or (M–H)$^+$ was determined on a Finnegan SSQ7000. High resolution mass spectra were determined on a Finnegan MAT900. Liquid chromatography (LC)/mass spectra were run on a Shimadzu LC coupled to a Water Micromass ZQ.

The following abbreviations are used: DMSO (dimethylsulfoxide); TFA (trifluoroacetic acid); DAST [(diethylamino)sulfur trifluoride]; HPLC (high pressure liquid chromatography); HCl (hydrochloric acid); LDA (lithium diisopropylamide); MgSO$_4$ (magnesium sulfate); BOC (tent-butyl dicarbonate); R.T. (retention time); rt (room temperature); aq. (aqueous).

Unless otherwise stated, LC/MS analyses were carried out on a Shimadzu instrument using a (A) Phenomenex-Luna 4.6×50 mm S10 reverse phase column employing a flow rate of 4 mL/min using a 0.1% TFA in methanol/water gradient [0-100% in 2 min, with 3 min run time], (B) Phenomenex-Luna 4.6×50 mm S10 reverse phase column employing a flow rate of 4 mL/min using a 0.1% TFA in methanol/water gradient [0-100% in 3 min, with 4 min run time], or (C) a Phenomenex-Luna 3.0×50 mm S10 reverse phase column employing a flow rate of 4 mL/min using a 0.1% TFA in methanol/water gradient [0-100% in 3 min, with 4 min run time], both with a uv detector set at 220 nm. Unless otherwise stated, analytical HPLC analyses were carried out on a Zorbax SB-C18 4.6×75 mm column employing a flow rate of 2.5 mL/min using a 0.2% H$_3$PO$_4$ in methanol/H$_2$O gradient [0-100% in 30 min, with 30 min run time, with a uv detector set at 220 nm. Preparative HPLC was carried out on a Phenomenex-Luna 30×100 mm S10 reverse phase column employing a flow rate of 30 mL/min and using a 0.1% TFA in methanol/water gradient of 0-100% in 6 min, with 10 min run time and a uv detector set at 220 nm. Unless otherwise stated, chiral LC analyses were carried out on a Chiralcel OJ 4.6×250 mm, 10µ column, employing a flow rate of 2 ml/min and using 12% ethanol/heptane at 35° C.

Exemplification of Reaction Scheme 1

Example 1

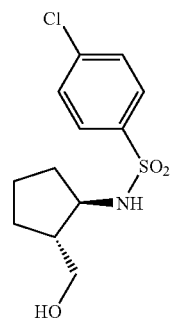

4-Chloro-N-(trans-2-hydroxymethylcyclopentyl)benzenesulfonamide

To a solution of trans-2-aminocyclopentylmethanol (prepared according to LaPlae et al., *J. Org. Chem.*, 66:5629-5632 (2001)) (1.05 g, 7.5 mmol) and triethylamine (1.25 mL, 9.0 mmol) in 25 mL tetrahydrofuran was added 4-chlorobenzenesulfonyl chloride (1.90 g, 9.0 mmol). The reaction was stirred at room temperature for 2 h, then diluted into 100 mL ethyl acetate and extracted with brine (50 mL). The organic layer was concentrated and purified by flash chromatography on a 40 g silica gel column using a gradient of 20 to 80% ethyl acetate in hexane over 30 min to give 4-chloro-N-(trans-2-hydroxymethylcyclopentyl)benzenesulfonamide (1.61 g, 74%). $^1$H NMR (400 MHz, CDCl$_3$) δ ppm 7.77-7.85 (2H, m), 7.42-7.52 (2H, m), 5.10 (1H, d, J=6.29 Hz), 3.70 (1H, ddd, J=10.64, 5.22, 5.04 Hz), 3.41-3.53 (1H, m), 3.21-3.33 (1H, m), 1.70-1.98 (4H, m), 1.44-1.68 (3H, m), 1.31-1.44 (1H, m). LC/MS R.T.=2.33 min; [M+H]$^+$=290.06.

Example 2

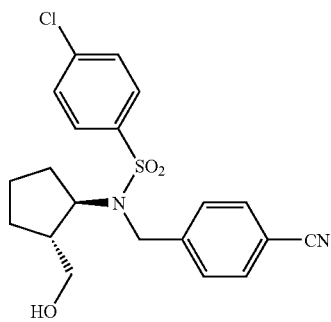

4-Chloro-N-(4-cyanobenzyl)-N-(trans-2-(hydroxymethyl)cyclopentyl)benzenesulfonamide A suspension of 4-chloro-N-(trans-2-hydroxymethylcyclopentyl)benzenesulfonamide (290 mg, 1.0 mmol), cesium-carbonate (652 mg, 2.0 mmol), and α-bromo-p-tolunitrile (253 mg, 1.2 mmol) in 2 mL dimethylformamide was stirred for 2 h. The reaction was diluted into 50 mL ethyl acetate and extracted with brine. The organic layer was concentrated and purified by flash chromatography on a 40 g silica gel column using a gradient of 20 to 70% ethyl acetate in hexane over 25 min. to give 4-chloro-N-(4-cyanobenzyl)-N-(trans-2-(hydroxymethyl)cyclopentyl)benzenesulfonamide (327 mg, 81%). $^1$H NMR (400 MHz, CDCl$_3$) δ ppm 7.71 (2H, d, J=8.56 Hz), 7.57-7.63 (2H, m), 7.49 (3H, dd, J=10.83, 8.31 Hz), 4.64 (1H, d, J=16.62 Hz), 4.16 (1H, d, J=16.62 Hz), 3.99-4.12 (1H, m), 3.37-3.62 (2H, m), 1.99 (1H, t, J=6.17 Hz), 1.32-1.71 (7H, m). LC/MS R.T.=2.77 min; [M+H]$^+$=404.12. HRMS [M+H]$^+$ calc'd 405.1040, found 405.1054.

Example 3

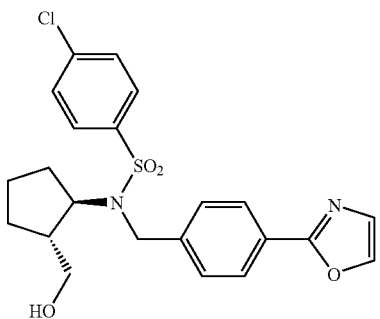

4-Chloro-N-(trans-2-(hydroxymethyl)cyclopentyl)-N-(4-(oxazol-2-yl)benzyl)benzenesulfonamide Compound 1

The title compound was synthesized from 4-chloro-N-(trans-2-hydroxymethylcyclopentyl)benzenesulfonamide (145 mg, 0.5 mmol), cesium carbonate (326 mg, 1.0 mmol), and 2-(4-(bromomethyl)phenyl)oxazole (143 mg, 0.6 mmol) according to the procedure described for 4-chloro-N-(4-cyanobenzyl)-N-(trans-2-(hydroxymethyl)cyclopentyl)benzenesulfonamide (Example 2) to give 4-chloro-N-(trans-2-(hydroxymethyl)cyclopentyl)-N-(4-(oxazol-2-yl)benzyl) benzenesulfonamide (178 mg, 80%). $^1$H NMR (400 MHz, CDCl$_3$) δ ppm 7.99 (2H, d, J=8.31 Hz), 7.66-7.78 (3H, m), 7.43-7.50 (4H, m), 7.22 (1H, s), 4.70 (1H, d, J=16.12 Hz), 4.15 (1H, d, J=16.12 Hz), 3.97-4.08 (1H, m), 3.57 (1H, dd, J=11.58, 4.28 Hz), 3.42 (1H, dd, J=11.46, 3.65 Hz), 1.34-1.71 (8H, m). LC/MS R.T.=2.14 min; [M+H]$^+$=447.12. HRMS [M+H]$^+$ calc'd 447.1145, found 447.1139.

Example 4

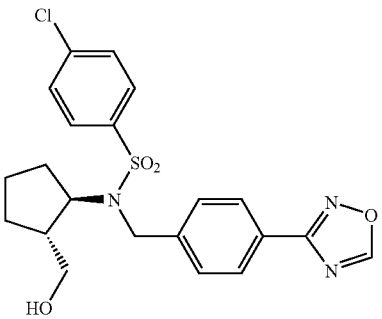

N-(4-(1,2,4-Oxadiazol-3-yl)benzyl)-4-chloro-N-(trans-2-(hydroxymethyl)cyclopentyl)benzenesulfonamide Compound 2

A solution of 4-chloro-N-(4-cyanobenzyl)-N-(trans-2-(hydroxymethyl)cyclopentyl)benzenesulfonamide (211 mg, 0.521 mmol) and 50% aqueous hydroxylamine (250 uL) was refluxed in ethanol (7 mL) overnight. The reaction was concentrated to dryness by rotary evaporation and co-evaporation with benzene. The dry amideoxime intermediate was then refluxed in triethylorthoformate (8 mL) under nitrogen for 5 h. After cooling to room temperature, boron trifluoride etherate (approximately 250 uL) was added and the reaction stirred overnight. The reaction was partitioned between ethyl acetate (25 mL) and brine (25 mL). The organic layer was concentrated and purified by flash chromatography on a 40 g silica gel column using a gradient of 10 to 60% ethyl acetate in hexane over 50 min to give N-(4-(1,2,4-oxadiazol-3-yl)benzyl)-4-chloro-N-(trans-2-(hydroxymethyl)cyclopentyl)benzenesulfonamide (118 mg, 51%). $^1$H NMR (400 MHz, CDCl$_3$) δ ppm 8.75 (1H, s), 8.03 (2H, d), 7.70 (2H, d, J=8.56 Hz), 7.48 (2H, d, J=8.31 Hz), 7.43 (2H, d, J=8.56 Hz), 4.67 (1H, d, J=16.37 Hz), 4.106 (1H, d, J=16.37 Hz), 3.93-4.06 (1H, m), 3.33-3.61 (2H, m), 1.28-1.75 (8H, m). LC/MS R.T.=2.90 min; [M+H]$^+$=448.16. HRMS [M+H]$^+$ calc'd 448.1098, found 448.1087.

Exemplification of Reaction Scheme 2

Example 5

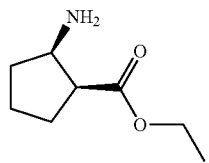

cis-Ethyl 2-aminocyclopentanecarboxylate

A solution of cis-ethyl 2-(benzylamino)cyclopentanecarboxylate (2.99 g, 12.1 mmol), prepared according to Bartoli, G. et al., *J. Org. Chem.*, 59:5328-5335, was hydrogenated along with 500 mg 10% palladium on carbon in 20 mL ethanol at 45 psi for 22 h. The reaction was filtered through a 45μ filter and concentrated to give cis-ethyl 2-aminocyclopentanecarboxylate (1.75 g, 92%). $^1$H NMR (400 MHz, CDCl$_3$) δ ppm 4.14 (2H, q, J=7.13 Hz), 3.53-3.62 (1H, m), 2.75 (1H, td, J=8.37, 6.67 Hz), 1.93-2.11 (1H, m), 1.77-1.92 (3H, m), 1.43-1.62 (2H, m), 1.35 (2H, s), 1.25 (3H, t, J=7.18 Hz). MS [M+H]$^+$=158.24.

Example 6

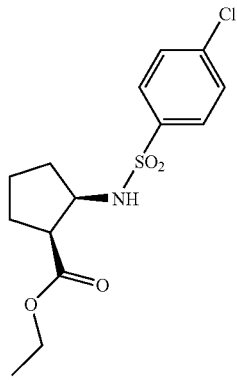

cis-Ethyl 2-(4-chlorophenylsulfonamido)cyclopentanecarboxylate

To a solution of cis-ethyl 2-aminocyclopentanecarboxylate (1.57 g, 10 mmol) in 50 mL tetrahydrofuran was added 4-chlorobenzenesulfonyl chloride (3.17 g, 15 mmol) and triethylamine (2.1 mL, 15 mmol). The reaction was stirred at room temperature for 4 h, then diluted into 100 mL diethyl ether and washed with 100 mL water. The organic layer was concentrated and purified by flash chromatography on a 120 g silica gel column with 10 to 40% ethyl acetate in hexane, 20 min gradient, to yield cis-ethyl 2-(4-chlorophenylsulfonamido)cyclopentanecarboxylate (3.05 g, 92%). $^1$H NMR (400 MHz, CDCl$_3$) δ ppm 7.76-7.80 (2H, m), 7.43-7.47 (2H, m), 5.57 (1 H, d, J=8.56 Hz), 3.91-4.10 (2H, m), 3.70-3.81 (1H, m), 2.74 (1H, dt, J=8.31, 6.55 Hz), 1.64-1.98 (5H, m), 1.44-1.58 (1H, m), 1.18 (3H, t, J=7.05 Hz). LC/MS R.T.=2.00 min; [M+H]$^+$=332.07; [M+Na]$^+$=354.04.

Example 7

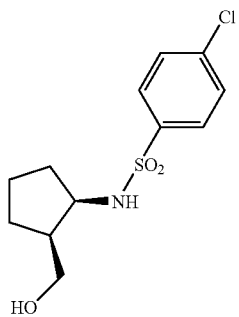

4-Chloro-N-(cis-2-(hydroxymethyl)cyclopentyl)benzenesulfonamide

A 1.0 M solution of lithium aluminum hydride in tetrahydrofuran (9.36 mL, 9.36 mmol) was added dropwise to a solution of cis-ethyl 2-(4-chlorophenylsulfonamido)cyclopentanecarboxylate (2.07 g, 6.24 mmol) in 40 mL anhydrous tetrahydrofuran under nitrogen at 0° C. The reaction was then stirred for 1 h at room temperature, then quenched by the slow addition of 100 mL ethyl acetate. The reaction was partitioned between 600 mL ethyl acetate and 300 mL saturated ammonium chloride. The organic layer was dried on sodium sulfate and concentrated to yield 4-chloro-N-(cis-2-(hydroxymethyl)cyclopentyl)benzenesulfonamide (1.81 g, 100%). $^1$H NMR (400 MHz, CDCl$_3$) δ ppm 7.77-7.85 (2H, m), 7.45-7.50 (2H, m), 5.38 (1H, d, J=7.05 Hz), 3.61-3.78 (3H, m), 2.04-2.15 (1H, m), 1.27-1.80 (7H, m). LC/MS R.T.=2.46 min; [M+H]$^+$=290.10.

Example 8

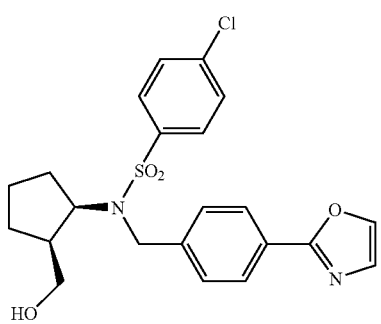

4-Chloro-N-(cis-2-(hydroxymethyl)cyclopentyl)-N-(4-(oxazol-2-yl)benzyl)benzenesulfonamide Compound 3

The title compound was synthesized from 4-chloro-N-(cis-2-(hydroxymethyl)cyclopentyl)benzenesulfonamide 145 mg, 0.50 mmol), cesium carbonate (326 mg, 1.0 mmol), and 2-(4-(bromomethyl)phenyl)oxazole (143 mg, 0.60 mmol) according to the procedure described for 4-chloro-N-(4-cyanobenzyl)-N-(trans-2-(hydroxymethyl)cyclopentyl)benzenesulfonamide (Example 2) to give 4-chloro-N-(cis-2-(hydroxymethyl)cyclopentyl)-N-(4-(oxazol-2-yl)benzyl)benzenesulfonamide (117 mg, 52%). $^1$H NMR (400 MHz, CDCl$_3$) δ ppm 7.94 (2H, d, J=8.31 Hz), 7.63-7.69 (3H, m), 7.33-7.44 (4H, m), 7.19 (1H, s), 4.62 (1H, d, J=16.62 Hz), 4.34 (1H, d, J=16.87 Hz), 4.19 (1H, q, J=7.47 Hz), 3.52 (1H, dd, J=11.21, 6.92 Hz), 3.33 (1H, dd, J=11.33, 5.54 Hz), 2.37-2.63 (1H, m), 2.09-2.25 (1H, m), 1.38-1.74 (5H, m), 1.15-1.30 (1H, m). LC/MS R.T.=2.76 min; [M+H]$^+$=447.20. HRMS [M+H]$^+$ calc'd 447.1145, found 447.1137.

Example 9

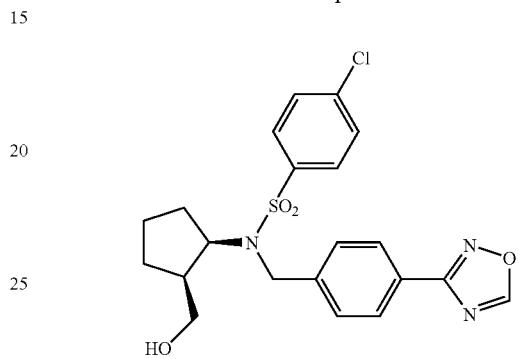

N-(4-(1,2,4-Oxadiazol-3-yl)benzyl)-4-chloro-N-(cis-2-(hydroxymethyl)cyclopentyl)benzenesulfonamide Compound 4

The title compound was synthesized from 4-chloro-N-(cis-2-(hydroxymethyl)cyclopentyl)benzenesulfonamide 145 mg, 0.50 mmol), cesium carbonate (326 mg, 1.0 mmol), and 3-(4-(bromomethyl)phenyl)-1,2,4-oxadiazole (143 mg, 0.60 mmol) according to the procedure described for 4-chloro-N-(4-cyanobenzyl)-N-(trans-2-(hydroxymethyl)cyclopentyl)benzenesulfonamide (Example 2) to give N-(4-(1,2,4-oxadiazol-3-yl)benzyl)-4-chloro-N-(cis-2-(hydroxymethyl)cyclopentyl)benzenesulfonamide (30 mg, 13%). $^1$H NMR (400 MHz, CDCl$_3$) δ ppm 8.74 (1H, s), 8.04 (2H, d, J=8.31 Hz), 7.68-7.73 (2H, m), 7.40-7.46 (4H, m), 4.66 (1H, d, J=16.87 Hz), 4.38 (1H, d, J=16.87 Hz), 4.23 (1H, q, J=7.22 Hz), 3.55 (1H, dd, J=11.21, 7.18 Hz), 338 (1H, dd, J=11.33, 5.04 Hz), 2.13-2.28 (1H, m), 1.49-1.83 (5H, m), 1.19-1.29 (1H, m). LC/MS R.T.=2.15 min; [M+H]$^+$=448.14. HRMS [M+H]$^+$ calc'd 448.1098, found 448.1108.

Exemplification of Reaction Scheme 3

Example 10

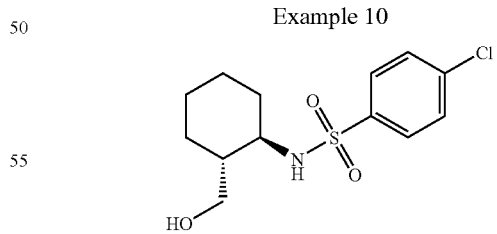

4-Chloro-N-(trans-2-(hydroxymethyl)cyclohexyl)benzenesulfonamide

To a suspension of trans-2-aminocyclohexylmethanol hydrochloride (4.50 g, 27.3 mmol) and triethylamine (11 mL, 81 mmol) in 200 mL dichloromethane at 0° C. was added dropwise a solution of 4-chlorobenzenesulfonyl chloride (5.69 g, 27.1 mmol) in 25 mL dichloromethane. The reaction was stirred at 0° C. for 1 h, then washed with aqueous sodium bicarbonate and water. The organic layer was concentrated and purified by flash chromatography on a 40 g silica gel column using a gradient of 0 to 100% ethyl acetate in hexane to give 4-chloro-N-(trans-2-hydroxymethylcyclohexyl)benzenesulfonamide (6.5 g, 78%). $^1$H NMR (400 MHz, CDCl$_3$) δ ppm 7.82 (m, 2H), 7.48 (m, 2H), 5.21 (d, J=7.81 Hz, 1H), 3.76-3.95 (m, 1H), 3.37 (ddd, J=11.14, 7.11, 3.40 Hz, 1H), 2.87-3.10 (m, 1H), 2.34-2.55 (m, 1 H), 1.47-1.70 (m, 4H), 1.19-1.40 (m, 2H), 0.94-1.19 (m, 3H). LC/MS R.T.=2.73 min; [M+H]$^+$=304. HRMS [M+H]$^+$ calc'd 304.0774, found 304.0768.

Example 11

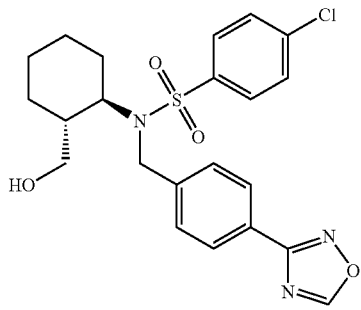

N-(4-(1,2,4-Oxadiazol-3-yl)benzyl)-4-chloro-N-(trans-2-(hydroxymethyl)cyclohexyl)benzenesulfonamide Compound 5

A suspension of 4-chloro-N-(trans-2-(hydroxymethyl)cyclohexyl)benzenesulfonamide (300 mg, 1.0 mmol), cesium carbonate (390 mg, 1.2 mmol), and 3-(4-(bromomethyl)phenyl)-1,2,4-oxadiazole (280 mg, 1.2 mmol) in dimethylformamide (5 mL) was stirred for 2 h. The reaction was concentrated and purified by flash chromatography on a 40 g silica gel column using a gradient of 0 to 80% ethyl acetate in hexane, then by preparative HPLC to give N-(4-(1,2,4-oxadiazol-3-yl)benzyl)-4-chloro-N-(trans-2-(hydroxymethyl)cyclohexyl)benzenesulfonamide (70 mg, 15%). $^1$H NMR (400 MHz, MeOD) δ ppm 9.23 (s, 1H), 8.00 (d, J=8.30 Hz, 2H), 7.75 (d, J=8.81 Hz, 2H), 7.54 (d, J=8.00 Hz, 2H), 7.51 (d, J=8.60 Hz, 2H), 4.55 (d, J=15.61 Hz, 1H), 4.36 (d, J=15.86 Hz, 1H), 3.52 (br. s., 1H), 3.31-3.38 (m, 1H), 3.14 (dd, J=11.08, 7.30 Hz, 1H), 1.87 (d, J=12.34 Hz, 1H), 1.53-1.75 (m, 2H), 1.30-1.53 (m, 3H), 0.98-1.22 (m, 3H). LC/MS R.T.=2.72 min; [M+H]$^+$=462. HRMS [M+H]$^+$ calc'd 462.1254, found 462.1241.

N-(4-(1,2,4-oxadiazol-3-yl)benzyl)-4-chloro-N-(trans-2-(hydroxymethyl)cyclohexyl)benzenesulfonamide (136 mg) was separated by preparative chiral SFC (Chiralcel OJ-H column, 30×250 mm, 12% ethanol, 60 ml/min, 35° C., 100 bar) to give the two trans enantiomers:

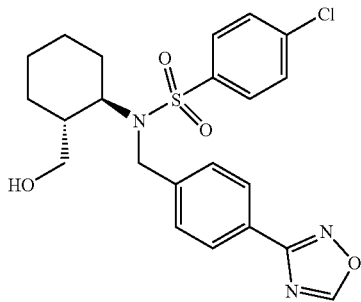

Peak A: Compound 6 Chiral LC: R.T.=13.09 min.
Peak B: Compound 7 Chiral LC: R.T.=16.53 min.

Example 12

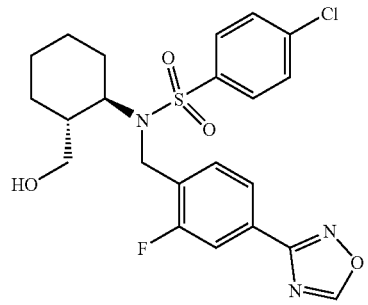

4-Chloro-N-(2-fluoro-4-(1,2,4-oxadiazol-3-yl)benzyl)-N-(trans-2-(hydroxymethyl)cyclohexyl)benzenesulfonamide Compound 8

The title compound was synthesized from 4-chloro-N-(trans-2-(hydroxymethyl)cyclohexyl)benzenesulfonamide (200 mg, 0.66 mmol), cesium carbonate (257 mg, 0.79 mmol), and 3-(4-(bromomethyl)-3-fluorophenyl)-1,2,4-oxadiazole (204 mg, 0.79 mmol) according to the procedure described for N-(4-(1,2,4-oxadiazol-3-yl)benzyl)-4-chloro-N-(trans-2-(hydroxymethyl)cyclohexyl)benzenesulfonamide (Example 11) to give 4-chloro-N-(2-fluoro-4-(1,2,4-oxadiazol-3-yl)benzyl)-N-(trans-2-(hydroxymethyl)cyclohexyl)benzenesulfonamide (75 mg, 24%). $^1$H NMR (400 MHz, CDCl$_3$) δ ppm 8.77 (s, 1H), 7.91 (dd, J=8.06, 1.51 Hz, 1H), 7.81 (t, J=7.81 Hz, 1H), 7.76 (d, J=10.20 Hz, 1H), 7.74 (d, J=8.60 Hz, 2H), 7.49 (d, J=8.60 Hz, 2H), 4.61 (d, J=15.86 Hz, 1H), 4.40 (d, J=15.61 Hz, 1H), 3.54-3.73 (m, 2H), 3.08 (dd, J=11.96, 1.64 Hz, 1H), 2.64 (br. s., 1H), 1.56-1.78 (m, 3H), 1.49 (ddd, J=12.21, 9.44, 9.32 Hz, 2H), 0.97-1.21 (m, 4H). Analytical HPLC R.T.=23.76 min. MS [M+H]$^+$=480; [M+Na]$^+$=502. HRMS [M+H]$^+$ calcd 480.1160, found 480.1157.

Example 13

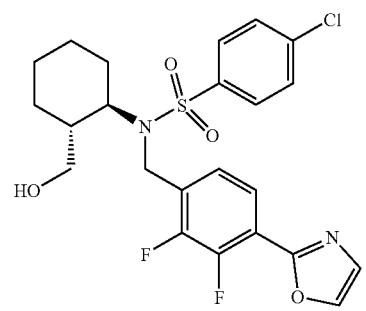

4-Chloro-N-(2,3-difluoro-4-(oxazol-2-yl)benzyl)-N-(trans-2-(hydroxymethyl)cyclohexyl)benzenesulfonamide Compound 9

The title compound was synthesized from 4-chloro-N-(trans-2-(hydroxymethyl)cyclohexyl)benzenesulfonamide (200 mg, 0.66 mmol), cesium carbonate (257 mg, 0.79 mmol), and 2-(4-(bromomethyl)-2,3-difluorophenyl)oxazole (217 mg, 0.79 mmol)) according to the procedure described for N-(4-(1,2,4-oxadiazol-3-yl)benzyl)-4-chloro-N-(trans-2-

(hydroxymethyl)cyclohexyl)benzenesulfonamide (Example 11) to give 4-chloro-N-(2,3-difluoro-4-(oxazol-2-yl)benzyl)-N-(trans-2-(hydroxymethyl)cyclohexyl)benzenesulfonamide (130 mg, 40%). $^1$H NMR (400 MHz, DMSO-$d_6$) δ ppm 8.35 (s, 1H), 7.83 (d, J=8.50 Hz, 2H), 7.80 (d, J=7.50 Hz, 1H), 7.64 (d, J=8.00 Hz, 2H), 7.45 (t, J=7.05 Hz, 1H), 4.52 (s, 2H), 3.41-3.52 (m, 1H), 3.29-3.40 (m, 1H), 3.25 (dd, J=10.45, 2.64 Hz, 1H), 2.80 (t, J=9.32 Hz, 1H), 1.95 (br. s., 1H), 1.52-1.60 (m, 2H), 1.38 (br. s., 3H), 1.18 (br. s., 1H), 0.86-1.04 (m, 2H). Analytical HPLC R.T.=23.46 min. MS $[M+H]^+$=497; $[M+Na]^+$=519. HRMS $[M+H]^+$ calc'd 497.1113, found 497.1093.

Example 14

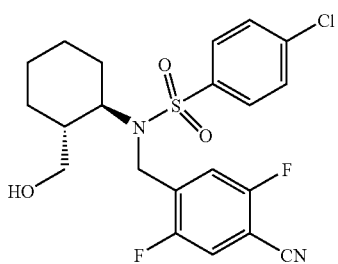

4-Chloro-N-(4-cyano-2,5-difluorobenzyl)-N-(trans-2-(hydroxymethyl)cyclohexyl)benzenesulfonamide Compound 10

The title compound was synthesized from 4-chloro-N-(trans-2-(hydroxymethyl)cyclohexyl)benzenesulfonamide (200 mg, 0.66 mmol), cesium carbonate (257 mg, 0.79 mmol), and 4-(bromomethyl)-2,5-difluorobenzonitrile (183 mg, 0.79 mmol) according to the procedure described for N-(4-(1,2,4-oxadiazol-3-yl)benzyl)-4-chloro-N-(trans-2-(hydroxymethyl)cyclohexyl)benzenesulfonamide (Example 11) to give 4-chloro-N-(4-cyano-2,5-difluorobenzyl)-N-(trans-2-(hydroxymethyl)cyclohexyl)benzenesulfonamide (130 mg, 43%). $^1$H NMR (400 MHz, CDCl$_3$) δ ppm 7.74 (m, 2H), 7.59 (dd, J=8.81, 5.79 Hz, 1H), 7.51 (m, 2H), 7.28 (dd, J=8.56, 5.04 Hz, 1H), 4.48 (d, J=13.00 Hz, 1H), 4.39 (d, J=14.00 Hz, 1H), 3.64 (td, J=11.58, 3.02 Hz, 1H), 3.55 (ddd, J=11.77, 4.72, 3.40 Hz, 1H), 3.15 (ddd, J=11.58, 9.19, 2.14 Hz, 1H), 2.41 (t, J=6.00 Hz, 1H), 1.68 (d, J=10.58 Hz, 3H), 1.30-1.52 (m, 2H), 0.98-1.19 (m, 4H). Analytical HPLC R.T.=23.37 min. MS $[M+H]^+$=455; $[M+Na]^+$=477.

Example 15

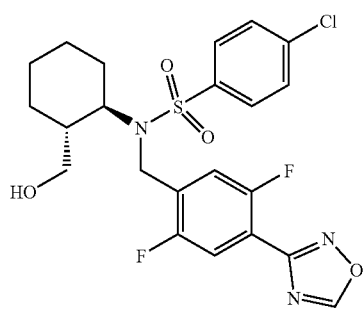

4-Chloro-N-(2,5-difluoro-4-(1,2,4-oxadiazol-3-yl)benzyl)-N-(trans-2-(hydroxymethyl)cyclohexyl)benzenesulfonamide Compound 11

A mixture of 4-chloro-N-(4-cyano-2,5-difluorobenzyl)-N-(trans-2-(hydroxymethyl)cyclohexyl)benzenesulfonamide (198 mg, 0.44 mmol), hydroxylamine hydrochloride (153 mg, 2.2 mmol), and triethylamine (300 uL, 2.2 mmol) was refluxed in 5 mL ethanol for 3 h. The reaction was concentrated and the residue was partitioned between ethyl acetate and sat. sodium bicarbonate solution. The organic layer was dried over magnesium sulfate and concentrated. The crude intermediate was stirred in 3 mL triethylorthoformate with two drops of boron trifluoride etherate at room temperature overnight. The reaction was purified by preparative HPLC followed by flash chromatography on silica gel with 0 to 60% ethyl acetate in hexane to yield 4-chloro-N-(2,5-difluoro-4-(1,2,4-oxadiazol-3-yl)benzyl)-N-(trans-2-(hydroxymethyl)cyclohexyl)benzenesulfonamide (100 mg, 46%). $^1$H NMR (400 MHz, CDCl$_3$) δ ppm 8.81 (s, 1H), 7.69-7.82 (m, 3H), 7.58 (dd, J=10.20, 5.92 Hz, 1H), 7.50 (d, J=8.56 Hz, 2H), 4.49-4.58 (m, 1H), 4.35-4.45 (m, 1H), 3.62-3.73 (m, 2H), 3.08-3.19 (m, 1H), 2.54 (br. s., 1H), 1.60-1.76 (m, 3H), 1.38-1.49 (m, 2H), 0.99-1.24 (m, 4H). Analytical HPLC R.T.=22.87 min. MS $[M+H]^+$=498; $[M+Na]^+$=520. HRMS $[M+H]^+$ calc'd 498.1066, found 498.1063.

Exemplification of Reaction Scheme 4

Example 16

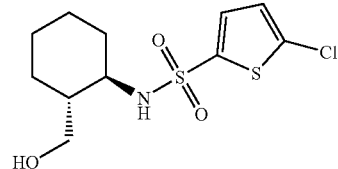

5-Chloro-N-(trans-2-(hydroxymethyl)cyclohexyl)thiophene-2-sulfonamide

To a suspension of trans-2-aminocyclohexylmethanol hydrochloride (214 mg, 1.30 mmol) and triethylamine (0.538 mL, 3.9 mmol) in 5 mL dichloromethane at 0° C. was added a solution of 5-chlorothiophene-2-sulfonyl chloride (0.267 mL, 1.23 mmol) in 1 mL dichloromethane. The reaction was stirred at 0° C. for 30 min and at room temperature for 30 min. The crude reaction mixture was purified by flash chromatography on silica gel using a gradient of 0 to 100% ethyl acetate in hexane to give 5-chloro-N-(trans-2-(hydroxymethyl)cyclohexyl)thiophene-2-sulfonamide (330 mg, 84%). $^1$H NMR (400 MHz, CDCl$_3$) δ ppm 7.40 (d, J=4.03 Hz, 1H), 6.91 (d, J=4.03 Hz, 1H), 5.24 (d, J=7.30 Hz, 1H), 3.86 (d, J=11.33 Hz, 1H), 3.32-3.48 (m, 1H), 3.05 (d, J=6.55 Hz, 1H), 2.32 (br. s., 1H), 1.72-1.83 (m, 1H), 1.58-1.73 (m, 3H), 1.11-1.36 (m, 5H). MS $[M+H]^+$=310; $[M+Na]^+$=332.

Example 17

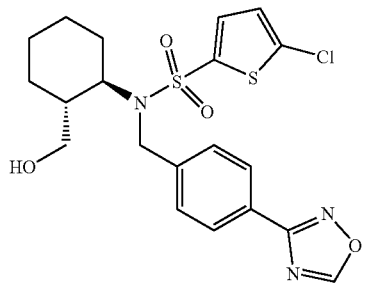

N-(4-(1,2,4-Oxadiazol-3-yl)benzyl)-5-chloro-N-(trans-2-(hydroxymethyl)cyclohexyl)thiophene-2-sulfonamide Compound 12

The title compound was synthesized from 5-chloro-N-(trans-2-(hydroxymethyl)cyclohexyl)thiophene-2-sulfonamide (100 mg, 0.32 mmol), cesium carbonate (126 mg, 0.39 mmol), and 3-(4-(bromomethyl)phenyl)-1,2,4-oxadiazole (93 mg, 0.39 mmol) according to the procedure described for N-(4-(1,2,4-oxadiazol-3-yl)benzyl)-4-chloro-N-(trans-2-(hydroxymethyl)cyclohexyl)benzenesulfonamide (Example 11) to give N-(4-(1,2,4-oxadiazol-3-yl)benzyl)-5-chloro-N-(trans-2-(hydroxymethyl)cyclohexyl)thiophene-2-sulfonamide (20 mg, 13%), $^1$H NMR (400 MHz, CDCl$_3$) δ ppm 8.75 (s, 1H), 8.07 (m, J=8.31 Hz, 2H), 7.54 (m, J=8.31 Hz, 2H), 7.30 (d, J=4.03 Hz, 1H), 6.91 (d, J=4.03 Hz, 1H), 4.72 (d, J=15.36 Hz, 1H), 4.16 (d, J=15.36 Hz, 1H), 3.60-3.65 (m, 1H), 3.68 (dd, J=11.96, 2.90 Hz, 1H), 3.09 (d, J=12.09 Hz, 1H), 1.70-1.80 (m, 1H), 1.66 (d, J=12.84 Hz, 1H), 1.36-1.61 (m, 4H), 1.12-1.28 (m, 1H), 0.92-1.09 (m, 2H). Analytical HPLC R.T.=21.54 min. MS [M+H]$^+$=468. HRMS [M+H]$^+$ calc'd 468.0819, found 468.0815.

Example 18

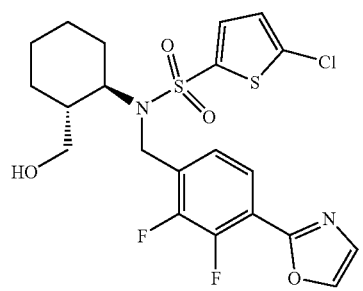

5-Chloro-N-(2,3-difluoro-4-(oxazol-2-yl)benzyl)-N-(trans-2-(hydroxymethyl)cyclohexyl)thiophene-2-sulfonamide Compound 13

The title compound was synthesized from 5-chloro-N-(trans-2-(hydroxymethyl)cyclohexyl)thiophene-2-sulfonamide (100 mg, 0.32 mmol), cesium carbonate (126 mmol, 0.39 mg), and 2-(4-(bromomethyl)-2,3-difluorophenyl)oxazole (93 mg, 0.39 mmol) according to the procedure described for N-(4-(1,2,4-oxadiazol-3-yl)benzyl)-4-chloro-N-(trans-2-(hydroxymethyl)cyclohexyl)benzenesulfonamide (Example 11) to give 5-chloro-N-(2,3-difluoro-4-(oxazol-2-yl)benzyl)-N-(trans-2-(hydroxymethyl)cyclohexyl) thiophene-2-sulfonamide (28 mg, 17%). $^1$H NMR (400 MHz, CDCl$_3$) δ ppm 7.78-7.84 (m, 1H), 7.79 (s, 1H), 7.50-7.57 (m, 1H), 7.37 (d, J=4.03 Hz, 1H), 7.32 (s, 1H), 6.95 (d, J=3.78 Hz, 1H), 4.58 (d, J=14.00 Hz, 1H), 4.42 (d, J=14.00 Hz, 1H), 3.53-3.73 (m, 2H), 2.98-3.19 (m, 1H), 2.38 (br. s., 1 H), 1.59-1.84 (m, 3H), 1.40-1.57 (m, 2H), 1.29-1.39 (m, 1H), 1.01-1.26 (m, 3H). Analytical HPLC R.T.=22.41 min. MS [M+H]$^+$=503. HRMS [M+H]$^+$ calc'd 503.0678, found 503.0654.

Exemplification of Reaction Scheme 5

Example 19

Separation of enantiomers of 4-chloro-N-(trans-2-(hydroxymethyl)cyclohexyl)benzenesulfonamide Racemic 4-chloro-N-(trans-2-(hydroxymethyl)cyclohexyl)benzenesulfonamide (2 g) (Scheme 3) was separated by chiral HPLC (Chiralpak AD column, 50×500 mm, 20μ, 50% heptane/IPA, 70 mL/min) to give both enantiomeric components:

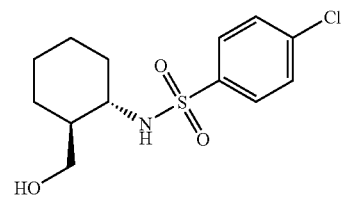

Peak A (0.87 g): Chiral LC (Chiralpak AD column, 4.6×250 mm, 10μ, 50% heptane/IPA): RT 4.55 min; 99.7% ee; [α]=−18.54° (CHCl$_3$) identified as 4-chloro-N-((1S,2S)-2-(hydroxymethyl)cyclohexyl)benzenesulfonamide (Compound 14) by inference, based on subsequent synthesis and single crystal X-ray structural determination of 4-chloro-N-(2,3-difluoro-4-(oxazol-2-yl)benzyl)-N-((1R,2R)-2-(hydroxymethyl)cyclohexyl)benzenesulfonamide.

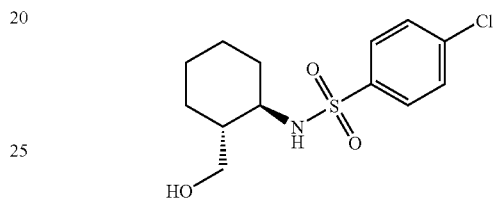

Peak B (0.85 g): (Chiralpak AD column, 4.6×250 mm, 10 μl, 50% heptane/IPA): RT 8.89 min; 99.9% ee, [α]=+17.53° (CHCl$_3$) identified as 4-chloro-N-((1R,2R)-2-(hydroxymethyl)cyclohexyl)benzenesulfonamide (Compound 15) by inference, based on subsequent synthesis and single crystal X-ray structural determination of 4-chloro-N-(2,3-difluoro-4-(oxazol-2-yl)benzyl)-N-((1R,2R)-2-(hydroxymethyl)cyclohexyl)benzenesulfonamide (Compound 16). $^1$H NMR (400 MHz, CDCl$_3$) δ ppm 7.82 (m, 2H), 7.48 (m, 2H), 5.21 (d, J=7.81 Hz, 1H), 3.76-3.93 (m, 1H), 3.37 (ddd, J=11.14, 7.11, 3.40 Hz, 1H), 2.89-3.08 (m, 1H), 2.33-2.54 (m, 1H), 1.51-1.75 (m, 4H), 1.18-1.35 (m, 2H), 0.93-1.18 (m, 3H).

Example 20

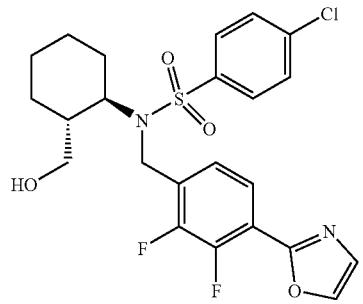

4-Chloro-N-(2,3-difluoro-4-(oxazol-2-yl)benzyl)-N-((1R,2R)-2-(hydroxymethyl)cyclohexyl)benzenesulfonamide Compound 16

A suspension of 4-chloro-N-((1R,2R)-2-(hydroxymethyl)cyclohexyl)benzenesulfonamide Compound 15 (130 mg, 0.43 mmol), cesium carbonate (167 mg, 0.51 mmol), and 2-(4-(bromomethyl)-2,3-difluorophenyl)oxazole (141 mg, 0.51 mmol) in dimethylformamide (2 mL) was stirred for 2 h. The reaction was partitioned between ethyl acetate and saturated sodium bicarbonate, dried over magnesium sulfate, concentrated and purified by flash chromatography on silica gel using a gradient of 0 to 100% ethyl acetate in hexane to give 4-chloro-N-(2,3-difluoro-4-(oxazol-2-yl)benzyl)-N-((1R,2R)-2-(hydroxymethyl)cyclohexyl)benzenesulfonamide (100 mg, 47%). Recrystallization from methanol yielded a crystalline product which was analyzed by X-Ray crystallography, verifying the stereochemistry as R,R. $^1$H NMR (400 MHz, CDCl$_3$) δ ppm 7.77-7.83 (m, 2H), 7.75 (m, 2H), 7.51-7.57 (m, 1H), 7.50 (m, 2H), 7.32 (s, 1H), 4.60 (d, J=15.86 Hz, 1H), 4.40 (d, J=15.86 Hz, 1H), 3.57-3.66 (m, 2H), 2.98-3.17 (m, 1H), 2.45-2.63 (m, 1H), 1.59-1.75 (m, 3H), 1.39-1.54 (m, 2H), 0.98-1.21 (m, 4H). MS [M+H]$^+$=497. HRMS [M+H]$^+$ calc'd 497.1113, found 497.1093. Chiral LC: R.T.=8.21 min, 100% ee.

Example 21

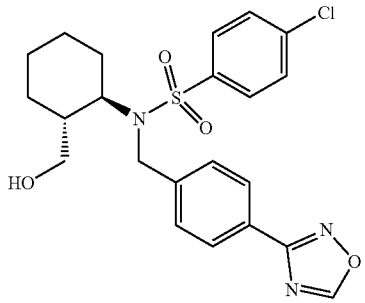

N-(4-(1,2,4-Oxadiazol-3-yl)benzyl)-4-chloro-N-((1R,2R)-2-(hydroxymethyl)cyclohexyl)benzenesulfonamide Compound 17

The title compound was synthesized from 4-chloro-N-((1R,2R)-2-(hydroxymethyl)cyclohexyl)benzenesulfonamide (28 mg, 0.09 mmol), cesium carbonate (36 mg, 0.11 mmol), and 3-(4-(bromomethyl)phenyl)-1,2,4-oxadiazole (26 mg, 0.11 mmol) according to the procedure described for 4-chloro-N-(2,3-difluoro-4-(oxazol-2-yl)benzyl)-N-((1R,2R)-2-(hydroxymethyl)cyclohexyl)benzenesulfonamide (Example 20) to give N-(4-(1,2,4-oxadiazol-3-yl)benzyl)-4-chloro-N-((1R,2R)-2-(hydroxymethyl)cyclohexyl)benzenesulfonamide (20 mg, 48%). MS [M+H]$^+$=462 HRMS [M+H]$^+$ calc'd 462.1254, found 462.1255. Chiral LC: R.T.=16.21 min., 98.0% ee.

Example 22

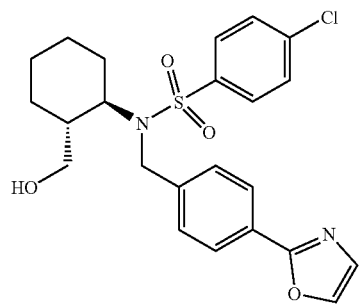

4-Chloro-N-((1R,2R)-2-(hydroxymethyl)cyclohexyl)-N-(4-(oxazol-2-yl)benzyl)benzenesulfonamide Compound 18

The title compound was synthesized from 4-chloro-N-((1R,2R)-2-(hydroxymethyl)cyclohexyl)benzenesulfonamide (100 mg, 0.33 mmol), cesium carbonate (129 mg, 0.40 mmol), and 2-(4-(bromomethyl)phenyl)oxazole (94 mg, 0.40 mmol) according to the procedure described for 4-chloro-N-(2,3-difluoro-4-(oxazol-2-yl)benzyl)-N-((1R,2R)-2-(hydroxymethyl)cyclohexyl)benzenesulfonamide (Example 20) to give 4-chloro-N-((1R,2R)-2-(hydroxymethyl)cyclohexyl)-N-(4-(oxazol-2-yl)benzyl)benzenesulfonamide (21 mg, 13%). $^1$H NMR (400 MHz, CDCl$_3$) δ ppm 7.98 (d, J=8.31 Hz, 2H), 7.70 (d, J=8.00 Hz, 3H), 7.43-7.51 (m, 4H), 7.23 (s, 1H), 4.73 (d, J=15.11 Hz, 1H), 4.09 (d, J=15.00 Hz, 1H), 3.66-3.81 (m, 2H), 3.07 (t, J=10.83 Hz, 1H), 2.62 (br. s., 1H), 1.62-1.73 (m, 1H), 1.37-1.62 (m, 4H), 1.06-1.28 (m, 2H), 0.81-1.06 (m, 2H). Analytical HPLC R.T.=22.99 min. MS [M+H]$^+$=461. HRMS [M+H]$^+$ calc'd 461.1302, found 461.1283. Chiral LC: R.T.=18.97 min., >98% ee.

Example 23

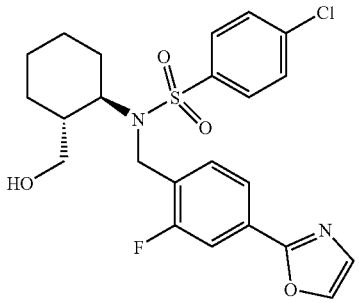

4-Chloro-N-(2-fluoro-4-(oxazol-2-yl)benzyl)-N-((1R,2R)-2-(hydroxymethyl)cyclohexyl)benzenesulfonamide Compound 19

The title compound was synthesized from 4-chloro-N-((1R,2R)-2-(hydroxymethyl)cyclohexyl)benzenesulfonamide (100 mg, 0.33 mmol), cesium carbonate (129 mg, 0.40 mmol), and 2-(4-(bromomethyl)-3-fluorophenyl)oxazole (101 mg, 0.40 mmol) according to the procedure described for 4-chloro-N-(2,3-difluoro-4-(oxazol-2-yl)benzyl)-N-((1R,2R)-2-(hydroxymethyl)cyclohexyl)benzenesulfonamide (Example 20) to give 4-chloro-N-(2-fluoro-4-(oxazol-2-yl)benzyl)-N-((1R,2R)-2-(hydroxymethyl)cyclohexyl)benzenesulfonamide (22 mg, 14%). $^1$H NMR (400 MHz, CDCl$_3$) δ ppm 7.63-7.86 (m, 6H), 7.44-7.51 (m, 2H), 7.24 (s, 1H), 4.60 (d, J=15.61 Hz, 1H), 4.38 (d, J=15.00 Hz, 1H), 3.63 (ddd, J=11.83, 4.78, 3.02 Hz, 2H), 3.00-3.11 (m, 1H), 2.57 (br. s., 1H), 1.55-1.70 (m, 3H), 1.43-1.54 (m, 2H), 0.95-1.19 (m, 4H). Analytical HPLC R.T.=23.89 min. MS [M+H]$^+$=479. HRMS [M+H]$^+$ calc'd 479.1208, found 479.1219. Chiral LC: R.T.=9.98 min., >98% ee.

Example 24

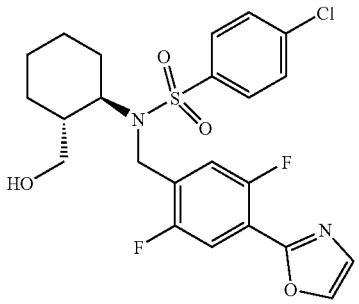

4-Chloro-N-(2,5-difluoro-4-(oxazol-2-yl)benzyl)-N-((1R,2R)-2-(hydroxymethyl)cyclohexyl)benzenesulfonamide Compound 20

The title compound was synthesized from 4-chloro-N-((1R,2R)-2-(hydroxymethyl)cyclohexyl)benzenesulfonamide (90 mg, 0.30 mmol), cesium carbonate (117 mg, 0.36 mmol), and 2-(4-(bromomethyl)-2,5-difluorophenyl)oxazole (99 mg, 0.36 mmol) according to the procedure described for 4-chloro-N-(2,3-difluoro-4-(oxazol-2-yl)benzyl)-N-((1R,2R)-2-(hydroxymethyl)cyclohexyl)benzenesulfonamide (Example 20) to give 4-chloro-N-(2,5-difluoro-4-(oxazol-2-yl)benzyl)-N-((1R,2R)-2-(hydroxymethyl)cyclohexyl)benzenesulfonamide (46 mg, 31%). $^1$H NMR (400 MHz, CDCl$_3$) δ ppm 7.77 (s, 1H), 7.74 (d, J=8.56 Hz, 2H), 7.68 (dd, J=9.95, 5.67 Hz, 1H), 7.52 (dd, J=9.95, 5.67 Hz, 1H), 7.49 (d, J=8.56 Hz, 2H), 7.29 (s, 1H), 4.52 (d, J=16.00 Hz, 1H), 4.37 (d, J=16.00 Hz, 1H), 3.53-3.65 (m, 2H), 3.12 (d, J=11.08 Hz, 1H), 2.57 (d, J=1.01 Hz, 1H), 1.58-1.77 (m, 3H), 1.36-1.53 (m, 2H), 0.98-1.21 (m, 4H). Analytical HPLC R.T.=22.02 min. MS [M+H]$^+$=497. HRMS [M+H]$^+$ calc'd 497.1113, found 497.1100.

Example 25

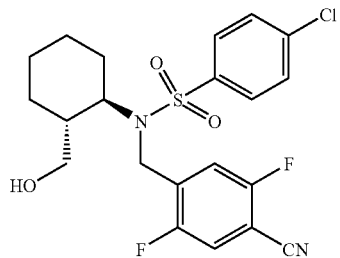

4-Chloro-N-(4-cyano-2,5-difluorobenzyl)-N-((1R,2R)-2-(hydroxymethyl)cyclohexyl)benzenesulfonamide The title compound was synthesized from 4-chloro-N-((1R,2R)-2-(hydroxymethyl)cyclohexyl)benzenesulfonamide (300 mg, 1.0 mmol), cesium carbonate (390 mg, 1.20 mmol), and 4-(bromomethyl)-2,5-difluorobenzonitrile (278 mg, 1.20 mmol) according to the procedure described for 4-chloro-N-(2,3-difluoro-4-(oxazol-2-yl)benzyl)-N-((1R,2R)-2-(hydroxymethyl)cyclohexyl)benzenesulfonamide (Example 20) to give 4-chloro-N-(4-cyano-2,5-difluorobenzyl)-N-((1R,2R)-2-(hydroxymethyl)cyclohexyl)benzenesulfonamide (350 mg, 77%). $^1$H NMR (400 MHz, CDCl$_3$) δ ppm 7.74 (m, 2H), 7.59 (dd, J=8.81, 5.79 Hz, 1H), 7.51 (m, 2H), 7.28 (dd, J=8.69, 4.91 Hz, 1H), 4.48 (d, J=15.80 Hz, 1H), 4.39 (d, J=15.80 Hz, 1H), 3.64 (ddd, J=14.00, 9.00, 4.00 Hz, 1H), 3.55 (ddd, J=11.83, 4.78, 3.53 Hz, 1H), 3.16 (ddd, J=11.52, 9.13, 2.27 Hz, 1H), 2.40 (br. s., 1H), 1.68 (d, J=10.58 Hz, 3H), 1.30-1.45 (m, 2H), 0.99-1.21 (m, 4H).

Example 26

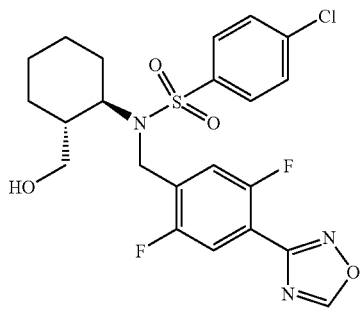

4-Chloro-N-(2,5-difluoro-4-(1,2,4-oxadiazol-3-yl)benzyl)-N-((1R,2R)-2-(hydroxymethyl)cyclohexyl)benzenesulfonamide Compound 21

A mixture of 4-chloro-N-(4-cyano-2,5-difluorobenzyl)-N-((1R,2R)-2-(hydroxymethyl)cyclohexyl)benzenesulfonamide (320 mg, 0.70 mmol) (Example 25), hydroxylamine hydrochloride (247 mg, 3.5 mmol), and triethylamine (488 uL, 3.5 mmol) was refluxed in 8 mL ethanol for 3 h. The reaction was concentrated and the residue was partitioned between ethyl acetate and sat. sodium bicarbonate solution. The organic layer was dried over magnesium sulfate and concentrated. The crude intermediate was stirred in 5 mL triethylorthoformate with three drops of boron trifluoride etherate at room temperature overnight. The reaction was purified by flash chromatography on silica gel with 0 to 60% ethyl acetate in hexane to yield 4-chloro-N-(2,5-difluoro-4-(1,2,4-oxadiazol-3-yl)benzyl)-N-((1R,2R)-2-(hydroxymethyl)cyclohexyl)benzenesulfonamide (250 mg, 71%). $^1$H NMR (400 MHz, CDCl$_3$) δ ppm 8.81 (s, 1H), 7.70-7.79 (m, 3H), 7.58 (dd, J=10.20, 5.92 Hz, 1H), 7.50 (d, J=8.56 Hz, 2H), 4.54 (d, J=15.60 Hz, 1H), 4.41 (d, J=15.60 Hz, 1H), 3.64 (td, J=7.93, 3.78 Hz, 2H), 3.14 (t, J=10.58 Hz, 1H), 2.52 (br. s., 1H), 1.58-1.74 (m, 3H), 1.45-1.53 (m, 2H), 1.02-1.26 (m, 4H). Analytical HPLC R.T.=22.92 min. MS [M+H]$^+$=498. HRMS [M+H] calc'd 498.1066, found 498.1087. Chiral LC: R.T.=9.84 min., 99% ee. Optical rotation: [α]=−36.66°, CHCl$_3$ (c=4.29 mg/mL).

Example 27

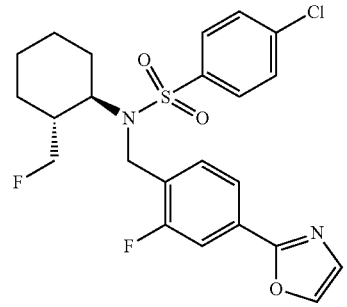

4-Chloro-N-(2-fluoro-4-(oxazol-2-yl)benzyl)-N-((1R,2R)-2-(fluoromethyl)cyclohexyl)benzenesulfonamide Compound 22

DAST (4-dimethylamino-N-methyl-4-stilbazolium tosylate, 9 μL, 0.06 mmol) was added to a solution of 4-chloro-N-(2-fluoro-4-(oxazol-2-yl)benzyl)-N-((1R,2R)-2-(hydroxymethyl)cyclohexyl)benzenesulfonamide (25 mg, 0.05 mmol) in 2 mL anhydrous methylene chloride at −20° C. The reaction was stirred at room temperature for 1 h, then purified by flash chromatography on silica gel with 0 to 50% ethyl acetate in hexane to yield 4-chloro-N-(2-fluoro-4-(oxazol-2-yl)benzyl)-N-((1R,2R)-2-(fluoromethyl)cyclohexyl)benzenesulfonamide (8 mg, 33%). $^1$H NMR (400 MHz, CDCl$_3$) δ ppm 7.82 (1H, dd, J=8.06, 1.51 Hz), 7.69-7.78 (4H, m), 7.67 (1H, dd, J=10.83, 1.51 Hz), 7.40-7.49 (2H, m), 7.23-7.26 (1H, m), 4.46 (2H, dd, J=34.50, 15.61 Hz), 3.97-4.22 (2H, m), 3.58 (1H, br. s.), 1.75-1.76 (1H, m), 1.59-1.74 (3H, m), 1.46 (2H, br. s.), 0.94-1.30 (3H, m). $^{19}$F NMR (376 MHz, CDCl$_3$) δ ppm −111.85 (s), −118.19 (s). Analytical HPLC R.T.=25.91 min. MS [M+H]$^{30}$ =481, [M+Na$^+$]=503. HRMS [M+H]$^+$ calc'd 481.1164, found 481.1176. Chiral LC: R.T.=6.08 min., >96% ee.

Exemplification of Reaction Scheme 6

Example 28

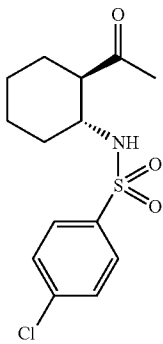

N-((1R,2R)-2-Acetylcyclohexyl)-4-chlorobenzene-sulfonamide

Benzyl (1R,2R)-2-acetylcyclohexylcarbamate (2.2 g, 8.00 mmol), 5% palladium on carbon (144 mg) and methanol (120 mL) were combined in a 250 mL round bottom flask. The mixture was flushed with nitrogen and then a hydrogen balloon was attached. The mixture was allowed to react for 20 min, at which time TLC indicated complete consumption of the starting material. The mixture was again flushed with nitrogen and filtered through celite to provide 1.1 g of a clear, colorless oil that was used directly in the next step without purification. Coupling of this intermediate with 4-chlorobenzene-1-sulfonyl chloride was done according to the procedure described for 5-chloro-N-(trans-2-(hydroxymethyl)cyclohexyl)thiophene-2-sulfonamide (Scheme 4) to give N-((1R,2R)-2-acetylcyclohexyl)-4-chlorobenzenesulfonamide as a clear oil (550 mg, 23% yield). $^1$H NMR (400 MHz, CDCl$_3$) δ ppm 7.70-7.83 (m, 2H), 7.41-7.52 (m, 2H), 5.06 (d, J=8.06 Hz, 1H), 3.30-3.42 (m, 1H), 2.38 (td, J=10.89, 3.65 Hz, 1H), 1.94-2.06 (m, 3H), 1.80-1.92 (m, 2H), 1.58-1.70 (m, 3H), 1.28-1.40 (m, 1H), 1.13-1.26 (m, 4H).

Example 29

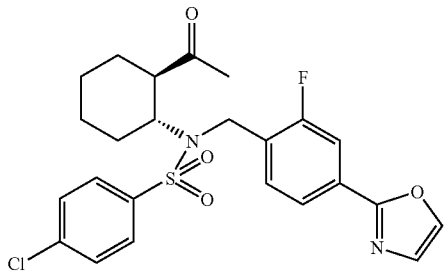

N-((1R,2R)-2-Acetylcyclohexyl)-4-chloro-N-(2-fluoro-4-(oxazol-2-yl)benzyl)benzenesulfonamide The title compound was synthesized from N-((1R,2R)-2-acetylcyclohexyl)-4-chlorobenzenesulfonamide as a clear oil (550 mg, 1.74 mmol), cesium carbonate (700 mg, 2.15 mmol), and 2-(4-(bromomethyl)-3-fluorophenyl)oxazole (513 mg, 2.00 mmol) according to the procedure described for 4-chloro-N-(2,3-difluoro-4-(oxazol-2-yl)benzyl)-N-((1R,2R)-2-(hydroxymethyl)cyclohexyl)benzenesulfonamide (Example 20) to give N-((1R,2R)-2-acetylcyclohexyl)-4-chloro-N-(2-fluoro-4-(oxazol-2-yl)benzyl) benzenesulfonamide as a clear oil (600 mg, 70% yield). $^1$H NMR (400 MHz, CDCl$_3$) δ ppm 7.66-7.78 (m, 4H), 7.63 (dd, J=10.83, 1.51 Hz, 1H), 7.51 (t, J=7.93 Hz, 1H), 7.36-7.43 (m, 2H), 7.21 (s, 1H), 4.41 (s, 2H), 3.93 (t, J=10.07 Hz, 1H), 2.74 (t, J=9.57 Hz, 1H), 1.79-1.91 (m, 4H), 1.58-1.71 (m, 3H), 1.43-1.55 (m, 1H), 1.10-1.22 (m, 3H).

Example 30

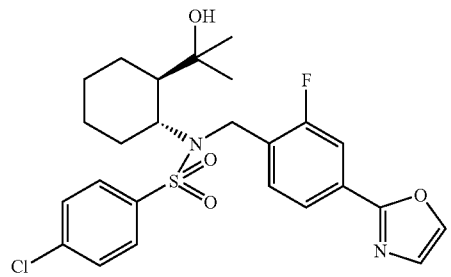

4-Chloro-N-(2-fluoro-4-(oxazol-2-yl)benzyl)-N-((1R,2R)-2-(2-hydroxypropan-2-yl)cyclohexyl)benzenesulfonamide Compound 23

N-((1R,2R)-2-acetylcyclohexyl)-4-chloro-N-(2-fluoro-4-(oxazol-2-yl)benzyl)benzenesulfonamide (150 mg, 0.31 mmol) was dissolved in tetrahydrofuran (5.0 mL) and a solution of 1.4M methyl magnesiumbromide in 3:1 toluene/tetrahydrofuran (2.0 mL, 2.8 mmol) was added. After 1 h, TLC indicated conversion to a new product. The reaction mixture was quenched with methanol followed by saturated aqueous ammonium chloride and extracted with ethyl acetate. The combined organics were dried over sodium sulfate, filtered and concentrated to give a mixture of starting material and product. The crude mixture was purified by flash chromatography on silica gel twice using a gradient of 15-50% ethyl acetate/hexanes followed by 10-35% ethyl acetate/hexanes to give 4-chloro-N-(2-fluoro-4-(oxazol-2-yl)benzyl)-N-((1R,2R)-2-(2-hydroxypropan-2-yl)cyclohexyl)benzenesulfonamide as a colorless oil (20 mg, 13% yield). $^1$H NMR (400 MHz, CDCl$_3$) δ ppm 7.66-7.78 (m, 4H), 7.62 (dd, J=10.83, 1.51 Hz, 1H), 7.52 (t, J=7.81 Hz, 1H), 7.35-7.45 (m, 2H), 7.21-7.28 (m, 3H), 4.44-4.56 (m, 2H), 3.87 (d, J=3.02 Hz, 1H), 3.06 (s, 1H), 1.85 (d, J=8.31 Hz, 2H), 1.62-1.69 (m, 2H), 1.52-1.61 (m, 3H), 1.49 (br. s., 1H), 1.18 (s, 3H), 1.05-1.16 (m, 7H). MS [M+H+Na]$^+$=529.19.

Example 31

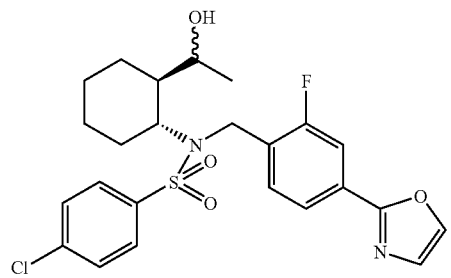

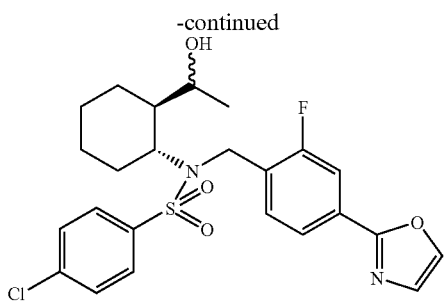

4-Chloro-N-(2-fluoro-4-(oxazol-2-yl)benzyl)-N-
((1R,2R)-2-(1-hydroxyethyl)cyclohexyl)benzene-
sulfonamide Compound 24 and 25

4-Chloro-N-(2-fluoro-4-(oxazol-2-yl)benzyl)-N-((1R,
2R)-2-(2-hydroxypropan-2-yl)cyclohexyl)benzenesulfona-
mide (150 mg, 0.31 mmol) was dissolved in tetrahydrofuran
(5.0 mL) and sodium borohydride (60 mg, 1.6 mmol) was
added. After 30 min, methanol (5.0 mL) was added. After an
additional 10 min, TLC indicated conversion to two new
products. The reaction mixture was quenched with saturated
aqueous ammonium chloride and extracted with ethyl
acetate. The combined organics were dried over sodium sul-
fate, filtered and concentrated to give a mixture of starting
material and product. The crude mixture was purified by
column chromatography on silica gel using a gradient of
15-50% ethyl acetate/hexanes to give both diastereomeric
components:

Peak A (50 mg, 33% yield) (Compound 24): The first peak
to elute. $^1$H NMR (400 MHz, CDCl$_3$) δ ppm 7.82-7.85 (m,
1H), 7.69-7.80 (m, 4H), 7.43-7.56 (m, 2H), 4.63 (d, J=15.36
Hz, 1H), 4.34 (d, J=15.36 Hz, 1H), 3.89-4.01 (m, 1H), 3.62
(br. s., 1H), 2.96 (br. s., 1H), 1.62-1.69 (m, 2H), 1.55-1.61 (m,
1H), 1.18-1.30 (m, 2H), 1.05-1.17 (m, 2H), 0.91-1.04 (m,
1H), 0.85 (d, J=7.05 Hz, 1H), 0.72 (d, J=6.80 Hz, 3H). MS
[M+H]$^+$=493. MS [M+Na]$^+$=515.

Peak B (54 mg, 36% yield) (Compound 25): The second
peak to elute. $^1$H NMR (400 MHz, CDCl$_3$) δ ppm 7.80-7.84
(m, 1H), 7.68-7.79 (m, 5H), 7.41-7.48 (m, 2H), 7.24 (d,
J=3.78 Hz, 2H), 4.48-4.55 (m, 1H), 3.84 (t, J=6.29 Hz, 1H),
1.79 (dd, J=9.19, 2.64 Hz, 1H), 1.66 (d, J=2.52 Hz, 1H), 1.47
(td, J=12.21, 3.53 Hz, 2H), 1.29-1.39 (m, 1H), 1.07-1.16 (m,
1H), 0.99-1.06 (m, 2H), 0.93-0.98 (m, 4H). MS [M+H]$^+$
=493. MS [M+Na]$^+$=515.

Exemplification of Reaction Scheme 7

Example 32

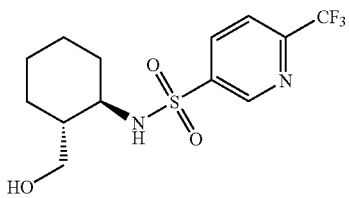

N-((1R,2R)-2-(Hydroxymethyl)cyclohexyl)-6-(trif-
luoromethyl)pyridine-3-sulfonamide A solution of 6-(trifluoromethyl)pyridine-3-sulfonyl chlo-
ride (190 mg, 0.78 mmol) in 2 mL dichloromethane was
added dropwise to a solution of ((1R,2R)-2-aminocyclo-
hexyl)methanol (100 mg, 0.78 mmol) and triethylamine (320
μL, 2.3 mmol) in 10 mL dichloromethane at 0° C. The reac-
tion was stirred at 0° C. for 1 h, then concentrated and purified
by flash chromatography on silica gel with 0 to 60% ethyl
acetate in hexane to yield N-((1R,2R)-2-(hydroxymethyl)cy-
clohexyl)-6-(trifluoromethyl)pyridine-3-sulfonamide (150
mg, 57%). $^1$H NMR (400 MHz, CDCl$_3$) δ ppm 9.18 (d, J=2.01
Hz, 1H), 8.37 (dd, J=8.06, 1.76 Hz, 1H), 7.83 (d, J=8.31 Hz,
1H), 5.83 (d, J=6.80 Hz, 1H), 3.77 (ddd, J=11.21, 3.78, 3.65
Hz, 1H), 3.36 (dt, J=11.33, 5.67 Hz, 1H), 2.97-3.15 (m, 1H),
2.37 (t, J=5.41 Hz, 1H), 1.73-1.87 (m, 1H), 1.67 (d, J=2.01
Hz, 1H), 1.56-1.66 (m, 2H), 1.33-1.46 (m, 1H), 1.05-1.30 (m,
4H). MS [M+H]$^+$=339. MS [M+Na]$^+$=361.

Example 33

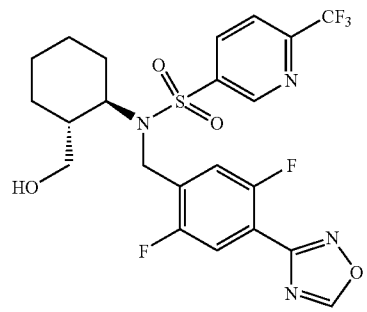

N-(2,5-Difluoro-4-(1,2,4-oxadiazol-3-yl)benzyl)-N-
((1R,2R)-2-(hydroxymethyl)cyclohexyl)-6-(trifluo-
romethyl)pyridine-3-sulfonamide Compound 26

The title compound was synthesized from N-((1R,2R)-2-
(hydroxymethyl)cyclohexyl)-6-(trifluoromethyl)pyridine-3-
sulfonamide (50 mg, 0.15 mmol), cesium carbonate (72 mg,
0.22 mmol), and 3-(4-(bromomethyl)-2,5-difluorophenyl)-1,
2,4-oxadiazole (50 mg, 0.18 mmol) according to the proce-
dure described for 4-chloro-N-(2,3-difluoro-4-(oxazol-2-yl)
benzyl)-N-((1R,2R)-2-(hydroxymethyl)cyclohexyl)
benzenesulfonamide (Example 20) to give N-(2,5-difluoro-
4-(1,2,4-oxadiazol-3-yl)benzyl)-N-(1R,2R)-2-
(hydroxymethyl)cyclohexyl)-6-(trifluoromethyl)pyridine-3-
sulfonamide (28 mg, 35%). $^1$H NMR (400 MHz, CDCl$_3$) δ
ppm 9.08 (d, J=2.01 Hz, 1H), 8.82 (s, 1H), 8.25 (dd, J=8.31,
2.01 Hz, 1H), 7.81 (d, J=8.31 Hz, 1H), 7.74 (dd, J=9.82, 5.54
Hz, 1H), 7.55 (dd, J=10.20, 5.92 Hz, 1H), 4.53 (d, J=15.50
Hz, 1H), 4.47 (d, J=15.60 Hz, 1H), 3.70-3.84 (m, 1H), 3.57
(dd, J=11.71, 2.90 Hz, 1H), 321 (d, J=11.58 Hz, 1H), 1.63-
1.81 (m, 3H), 1.43-1.56 (m, 2H), 1.33-1.41 (m, 1H), 1.16-
1.31 (m, 2H), 1.05-1.14 (m, 1H). Analytical HPLC
R.T=21.66. HRMS [M+H]$^+$ calc'd 533.1282, found
533.1277.

Example 34

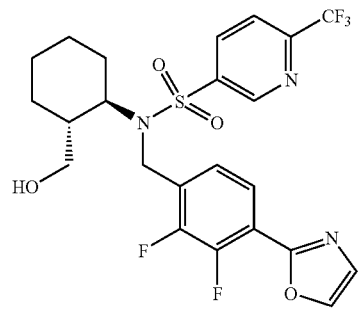

N-(2,3-Difluoro-4-(oxazol-2-yl)benzyl)-N-(trans-2-
(hydroxymethyl)cyclohexyl)-6-(trifluoromethyl)
pyridine-3-sulfonamide Compound 27

The title compound was synthesized from N-((1R,2R)-2-
(hydroxymethyl)cyclohexyl)-6-(trifluoromethyl)pyridine-3-
sulfonamide (50 mg, 0.15 mmol), cesium carbonate (72 mg, 0.22 mmol), and 2-(4-(bromomethyl)-2,3-difluorophenyl) oxazole (50 mg, 0.18 mmol) according to the procedure described for 4-chloro-N-(2,3-difluoro-4-(oxazol-2-yl)benzyl)-N-((1R,2R)-2-(hydroxymethyl)cyclohexyl)benzenesulfonamide (Example 20) to give N-(2,3-difluoro-4-(oxazol-2-yl)benzyl)-N-((1R,2R)-2-(hydroxymethyl)cyclohexyl)-6-(trifluoromethyl)pyridine-3-sulfonamide (41 mg, 52%). $^1$H NMR (400 MHz, CDCl$_3$) δ ppm 9.07 (d, J=2.01 Hz, 1H), 8.23 (dd, J=8.18, 1.89 Hz, 1H), 7.73-7.84 (m, 3H), 7.44-7.52 (m, 1H), 7.34 (s, 1H), 4.54-4.63 (m, 1H), 4.43-4.53 (m, 1H), 3.77 (td, J=11.58, 3.02 Hz, 1H), 3.60 (dd, J=11.96, 3.15 Hz, 1H), 3.21 (dd, J=11.83, 2.27 Hz, 1H), 3.16 (br. s., 1H), 1.63-1.80 (m, 3H), 1.40-1.61 (m, 2H), 1.35 (dd, J=11.71, 2.14 Hz, 1H), 1.04-1.28 (m, 3H). Analytical HPLC R.T.=22.34 min. HRMS [M+H]$^+$ calc'd 532.1329, found 532.1323.

Exemplification of Reaction Scheme 8

Example 35

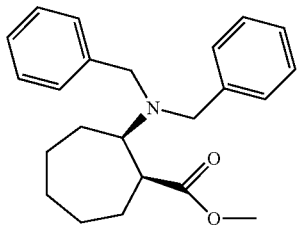

cis-Methyl 2-(dibenzylamino)cycloheptanecarboxylate

Benzyl bromide (7.13 mL, 60 mmol) was added to a stirring solution of cis-methyl-2-aminocycloheptanecarboxylate hydrochloride (2.08 g, 10 mmol) and diisopropylethylamine (6.53 mL, 37.5 mmol) in 20 mL DMF. The reaction was stirred at room temperature for 24 h, then diluted into 250 mL diethyl ether and extracted twice with 250 mL water. The diethyl ether layer was dried over sodium sulfate, concentrated, and purified by flash chromatography on 120 g silica gel with 0 to 20% ethyl acetate in hexane to yield cis-methyl 2-(dibenzylamino)cycloheptanecarboxylate (3.33 g, 95%). $^1$H NMR (400 MHz, CDCl$_3$) δ ppm 7.23-7.38 (8H, m), 7.15-7.22 (2H, m), 3.72 (2H, d, J=13.60 Hz), 3.64 (3H, s), 3.45 (2H, d, J=13.60 Hz), 3.18 (1H, ddd, j=11.21, 6.80, 4.66 Hz), 2.87 (1H, ddd, J=9.57, 6.67, 3.40 Hz), 1.95-2.02 (1H, m), 1.64-1.92 (6H, m), 1.27-1.39 (1H, m), 1.05-1.19 (2H, m). LC/MS R.T.=2.14 min; [M+H]$^+$=352.18.

Example 36

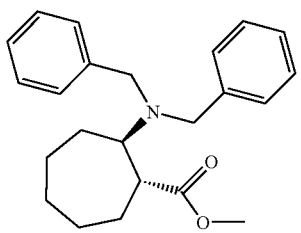

trans-Methyl 2-(dibenzylamino)cycloheptanecarboxylate

Potassium bis(trimethylsilyl)amide (31.7 mL, 15.9 mmol) was added dropwise to a solution of t-butanol in anhydrous tetrahydrofuran under nitrogen at room temperature. After 30 min, a solution of cis-methyl 2-(dibenzylamino)cycloheptanecarboxylate (1.33 g, 3.78 mmol) in 50 mL anhydrous tetrahydrofuran was added dropwise via syringe. The reaction was stirred for 17 h and then was partitioned between 250 mL diethyl ether and 200 mL brine. The organic layer was concentrated and purified by flash chromatography on 120 g silica gel with 2 to 4% ethyl acetate in hexane to yield trans-methyl 2-(dibenzylamino)cycloheptanecarboxylate (895 mg, 67%). $^1$H NMR (400 MHz, CDCl$_3$) δ ppm 7.23-7.30 (8H, m), 7.16-7.22 (2H, m), 3.77 (2H, d, J=13.60 Hz), 3.51 (3H, s), 3.26 (2H, d, J=13.35 Hz), 3.02 (1H, ddd, J=11.08, 8.81, 2.77 Hz), 2.77 (1H, ddd, J=11.02, 6.99, 4.41 Hz), 1.88-1.99 (1H, m), 1.28-1.83 (9H, m).

LC/MS R.T.=2.12 min; [M+H]$^+$=352.18.

Example 37

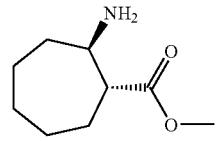

trans-Methyl-2-aminocycloheptanecarboxylate acetate trans-Methyl 2-(dibenzylamino)cycloheptanecarboxylate (1.04 g, 2.94 mmol) was hydrogenated at 50 psi in 20 mL glacial acetic acid with 500 mg 10% palladium on carbon for 25 h. The reaction was filtered through celite and concentrated to yield trans-methyl 2-aminocycloheptanecarboxylate acetate (500 mg, 99%). $^1$H NMR (400 MHz, CDCl$_3$) δ ppm 3.71 (3H, s), 3.35-3.44 (1H, m), 2.59 (1H, td, J=8.62, 3.15 Hz), 1.84-1.96 (2H, m), 1.61-1.80 (4H, m), 1.41-1.60 (4H, m). MS [M+H]$^+$=171.94.

Example 38

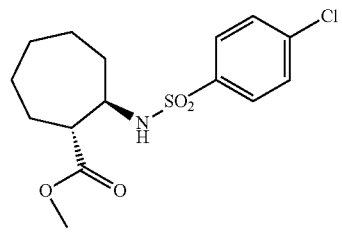

trans-Methyl 2-(4-chlorophenylsulfonamido)cycloheptanecarboxylate

A solution of trans-methyl 2-aminocycloheptanecarboxylate acetate (652 mg, 2.82 mmol), 4-chlorobenzene sulfonyl chloride (893 mg, 4.23 mmol), and triethylamine (1.18 mL, 8.46 mmol) was stirred in 20 mL tetrahydrofuran for 2 h. The reaction was partitioned between 100 mL diethyl ether and 100 mL brine. The organic layer was dried over sodium sulfate, concentrated, and purified by flash chromatography on 40 g silica gel with 15 to 40% ethyl acetate in hexane to yield trans-methyl 2-(4-chlorophenylsulfonamido)cycloheptanecarboxylate (253 mg, 26%). $^1$H NMR (400 MHz, CDCl$_3$) δ ppm 7.77-7.79 (1H, m), 7.74-7.76 (1H, m), 7.44-7.47 (1H, m), 7.42-7.44 (1H, m), 5.21 (1H, d, J=8.56 Hz), 3.68 (1H, qd, J=8.48, 3.78 Hz), 3.43 (3H, s), 2.44 (1H, td, J=8.56, 3.27 Hz), 1.75-1.82 (1H, m), 1.56-1.73 (4H, m), 1.34-1.54 (5H, m). LC/MS R.T.=2.89 min; [M−H]$^+$=344.04; [M+Na]$^+$=368.16; [M−H]$^-$=344.04.

Example 39

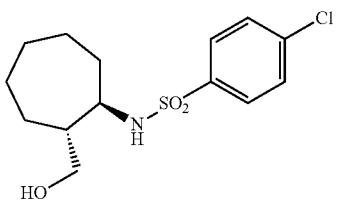

4-Chloro-N-(trans-2-(hydroxymethyl)cycloheptyl)benzenesulfonamide

A 1.0 M solution of lithium aluminum hydride in tetrahydrofuran (1.10 mL, 1.10 mmol) was added dropwise to a solution of trans-methyl 2-(4-chlorophenylsulfonamido)cycloheptanecarboxylate (253 mg, 0.73 mmol) in anhydrous tetrahydrofuran at −60° C. under nitrogen. The reaction was stirred at room temperature for 1.5 h and quenched by the addition of 25 mL ethyl acetate. The reaction was extracted twice with 25 mL saturated aqueous ammonium chloride. The organic layer was dried over sodium sulfate and concentrated to yield 4-chloro-N-(trans-2-(hydroxymethyl)cycloheptyl)benzenesulfonamide (216 mg, 93%). $^1$H NMR (400 MHz, CDCl$_3$) δ ppm 7.81-7.83 (1H, m), 7.79-7.80 (1H, m), 7.47-7.49 (1H, m), 7.44-7.46 (1H, m), 5.40 (1H, d, J=8.06 Hz), 3.64 (1H, dd, J=11.08, 4.78 Hz), 3.48 (1H, dd, J=10.95, 4.41 Hz), 3.15-3.27 (1H, m), 2.27 (1H, br. s.), 1.58-1.72 (2H, m), 1.42-1.55 (5H, m), 1.21-1.39 (4H, m). LC/MS R.T.=2.18 min; [M+H]$^+$=318.08; [M+Na]$^+$=340.09; [M−H]$^−$=316.07.

Example 40

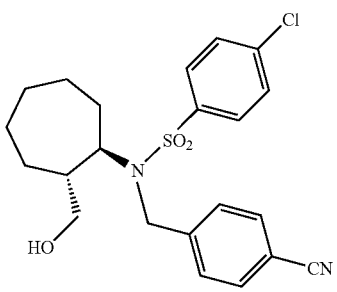

4-Chloro-N-(4-cyanobenzyl)-N-(trans-2-(hydroxymethyl)cycloheptyl)benzenesulfonamide Compound 28

A solution of 4-chloro-N-(trans-2-(hydroxymethyl)cycloheptyl)benzenesulfonamide (126 mg, 0.39 mmol), cesium carbonate (254 mg, 0.78 mmol), and 4-(bromomethyl)benzonitrile (92 mg, 0.47 mmol) was stirred in 2 mL dimethylformamide for 1.5 h. The reaction was partitioned between 25 mL diethyl ether and 25 mL 0.1 M HCl, concentrated and purified by flash chromatography on 40 g silica gel with 0 to 70% ethyl acetate in hexane to yield 4-chloro-N-(4-cyanobenzyl)-N-(trans-2-(hydroxymethyl)cycloheptyl)benzenesulfonamide (152 mg, 90%). $^1$H NMR (400 MHz, CDCl$_3$) δ ppm 7.73 (2H, d, J=8.31 Hz), 7.60-7.65 (2H, m), 7.54 (2H, d, J=8.31 Hz), 7.50 (2H, d, J=8.56 Hz), 4.65 (1H, d, J=16.12 Hz), 4.01 (1H, d, J=16.12 Hz), 3.76-3.88 (1H, m), 3.61-3.72 (1H, m), 3.28-3.41 (1H, m), 2.18 (1H, br. s.), 1.44-1.63 (5H, m), 1.11-1.40 (6H, m). LC/MS R.T.=2.76 min; [M+H]$^+$=433.14. HRMS [M+H]$^+$ calc'd 433.1353, found 433.1352.

Example 41

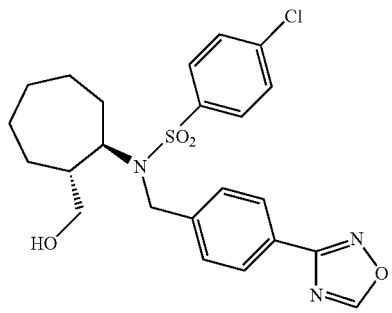

N-(4-(1,2,4-Oxadiazol-3-yl)benzyl)-4-chloro-N-(trans-2-(hydroxymethyl)cycloheptyl)benzenesulfonamide Compound 29

The title compound was synthesized from 4-chloro-N-(trans-2-(hydroxymethyl)cycloheptyl)benzenesulfonamide (100 mg, 0.32 mmol), cesium carbonate (205 mg, 0.63 mmol), and 3-(4-(bromomethyl)phenyl)-1,2,4-oxadiazole (90 mg, 0.38 mmol) according to the procedure described for 4-Chloro-N-(4-cyanobenzyl)-N-(trans-2-(hydroxymethyl)cycloheptyl)benzenesulfonamide (Example 40) to give N-(4-(1,2,4-oxadiazol-3-yl)benzyl)-4-chloro-N-(trans-2-(hydroxymethyl)cycloheptyl)benzenesulfonamide (50 mg, 33%). $^1$H NMR (400 MHz, CDCl$_3$) δ ppm 8.75 (1H, s), 8.08 (2H, d, J=8.31 Hz), 7.70-7.79 (2H, m), 7.55 (2H, d, J=8.31 Hz), 7.47-7.52 (2H, m), 4.73 (1H, d, J=15.86 Hz), 4.02 (1H, d, J=15.61 Hz), 3.82 (1H, ddd, J=11.14, 8.75, 3.02 Hz), 3.71 (1H, dd, J=11.71, 3.90 Hz), 3.31 (1H, dd, J=11.58, 2.52 Hz), 2.55 (1H, br. s.), 1.43-1.68 (6H, m), 1.17-1.42 (5H, m). LC/MS R.T.=2.29 min; [M+H]$^+$=476.18. HRMS [M+H]$^+$ calc'd 476.1411, found 476.1398.

Example 42

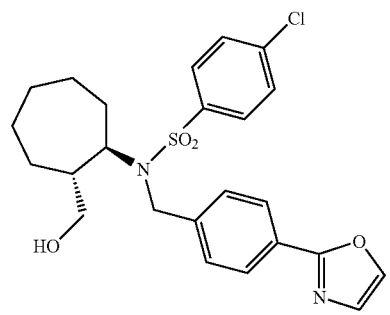

4-Chloro-N-(trans-2-(hydroxymethyl)cycloheptyl)-N-(4-(oxazol-2-yl)benzyl)benzenesulfonamide Compound 30

The title compound was synthesized from 4-chloro-N-(trans-2-(hydroxymethyl)cycloheptyl)benzenesulfonamide (80 mg, 0.25 mmol), cesium carbonate (164 mg, 0.50 mmol), and 2-(4-(bromomethyl)phenyl)oxazole (72 mg, 0.30 mmol) according to the procedure described for 4-Chloro-N-(4-cyanobenzyl)-N-(trans-2-(hydroxymethyl)cycloheptyl)benzenesulfonamide (Example 40) to give 4-chloro-N-(trans-2-(hydroxymethyl)cycloheptyl)-N-(4-(oxazol-2-yl)benzyl)

benzenesulfonamide (104 mg, 87%). $^1$H NMR (400 MHz, CDCl$_3$) δ ppm 7.99 (2H, d, J=8.31 Hz), 7.73-7.75 (1H, m), 7.71-7.73 (1H, m), 7.69 (1H, s), 7.51 (1H, s), 7.48 (2H, s), 7.44-7.47 (1H, m), 7.21 (1H, s), 4.69 (1H, d, J=15.86 Hz), 3.99 (1H, d, J=15.61 Hz), 3.74-3.85 (1H, m), 3.67 (1H, dd, J=11.58, 4.28 Hz), 3.28 (1H, dd, J=11.58, 2.27 Hz), 2.27 (1H, br. s.), 1.42-1.65 (6H, m), 1.12-1.39 (5H, m). LC/MS R.T.=2.25 min; [M+H]$^+$=475.22. HRMS [M+H]$^+$ calc'd 475.1458, found 475.1459.

Exemplification of Reaction Scheme 9

Example 43

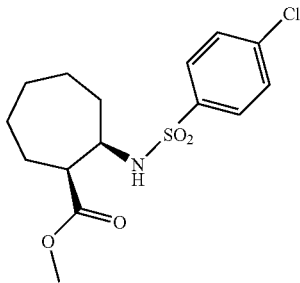

cis-Methyl 2-(4-chlorophenylsulfonamido)cycloheptanecarboxylate

4-Chlorobenzenesulfonylchloride (3.17 g, 15 mmol) was added to a mixture of cis-methyl 2-aminocycloheptanecarboxylate hydrochloride 2.08 g, 10 mmol) and triethylamine (4.2 mL, 30 mmol) and stirred at room temperature for 4 h. The reaction was partitioned between 100 mL diethyl ether and 100 mL water. The organic layer was dried over sodium sulfate, concentrated, and purified by flash chromatography on 120 g silica gel with 0 to 30% ethyl acetate in hexane to yield cis-methyl 2-(4-chlorophenylsulfonamido)cycloheptanecarboxylate (3.15 g, 91%). $^1$H NMR (400 MHz, CDCl$_3$) δ ppm 7.78-7.81 (1H, m), 7.74-7.78 (1H, m), 7.46-7.48 (1H, m), 7.42-7.46 (1H, m), 5.33 (1H, d, J=9.57 Hz), 3.59 (3H, s), 3.53 (1H, tt, J=9.57, 4.03 Hz), 2.80 (1H, dt, J=8.06, 4.03 Hz), 1.76-1.92 (2H, m), 1.44-1.75 (6H, m), 1.25-1.41 (2H, m). LC/MS R.T.=2.65 min; [M+H]$^+$=346.10; [M+Na]$^+$=368.07; [M−H]$^-$=344.04.

Example 44

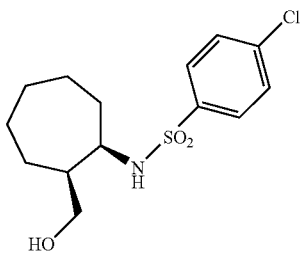

4-Chloro-N-(cis-2-(hydroxymethyl)cycloheptyl)benzenesulfonamide

A 1.0 M solution of lithium aluminum hydride in tetrahydrofuran (7.5 mL, 7.5 mmol) was added dropwise to a solution of cis-methyl 2-(4-chlorophenylsulfonamido)cycloheptanecarboxylate (1.73 g, 5.0 mmol) in 60 mL anhydrous tetrahydrofuran under nitrogen cooled to −60° C. The reaction was stirred for 1.5 h at room temperature and quenched by the slow addition of 150 mL ethyl acetate followed by 150 mL saturated aqueous ammonium chloride. The layers were separated and the aqueous layer was extracted an additional two times with 150 mL ethyl acetate. The combined organic layers were dried over sodium sulfate and concentrated to yield 4-chloro-N-(cis-2-(hydroxymethyl)cycloheptyl)benzenesulfonamide (1.55 g, 98%). $^1$H NMR (400 MHz, CDCl$_3$) δ ppm 7.82-7.84 (1H, m), 7.80-7.82 (1H, m), 7.48-7.50 (1H, m), 7.45-7.47 (1H, m), 5.13 (1H, d, J=9.57 Hz), 3.70-3.80 (1H, m), 3.61 (1H, dd, J=11.21, 10.20 Hz), 3.41 (1H, dd, J=11.46, 4.66 Hz), 2.69 (1H, br. s.), 1.67-1.83 (1H, m), 1.53-1.62 (2H, m), 1.26-1.51 (7H, m), 1.05-1.20 (1H, m).

Example 45

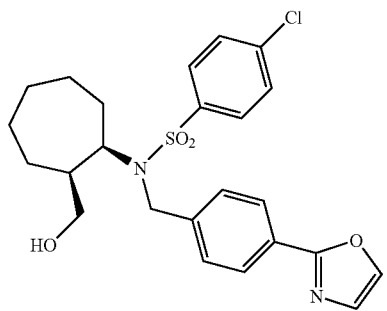

4-Chloro-N-(cis-2-(hydroxymethyl)cycloheptyl)-N-(4-(oxazol-2-yl)benzyl)benzenesulfonamide Compound 31

The title compound was synthesized from 4-chloro-N-(cis-2-(hydroxymethyl)cycloheptyl)benzenesulfonamide (119 mg, 0.38 mmol), cesium carbonate (244 mg, 0.75 mmol), and 2-(4-(bromomethyl)phenyl)oxazole (98 mg, 0.41 mmol) according to the procedure described for 4-chloro-N-(4-cyanobenzyl)-N-(trans-2-(hydroxymethyl)cyclopentyl)benzenesulfonamide (Example 40) to give 4-chloro-N-(cis-2-(hydroxymethyl)cycloheptyl)-N-(4-(oxazol-2-yl)benzyl)benzenesulfonamide (97 mg, 54%). $^1$H NMR (400 MHz, CDCl$_3$) δ ppm 7.95 (2H, d, J=8.31 Hz), 7.71 (1H, s), 7.66 (2H, d, J=8.56 Hz), 7.43 (4H, t, J=9.06 Hz), 7.26 (1H, s), 4.64 (1H, d, J=16.62 Hz), 4.41 (1H, d, J=16.62 Hz), 4.24-4.31 (1H, m), 3.57 (1H, dd, J=11.33, 8.31 Hz), 3.33 (1H, dd, J=11.33, 5.54 Hz), 1.90-2.05 (1H, m), 1.40-1.78 (6H, m), 1.11-1.34 (5H, m). LC/MS R.T.=2.21 min; [M+H]$^+$=475.11. HRMS [M+H]$^+$ calc'd 475.1458, found 475.1437.

Example 46

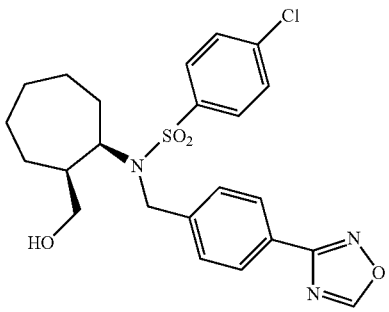

N-(4-(1,2,4-Oxadiazol-3-yl)benzyl)-4-chloro-N-(cis-2-(hydroxymethyl)cycloheptyl)benzenesulfonamide Compound 32

The title compound was synthesized from 4-chloro-N-(cis-2-(hydroxymethyl)cycloheptyl)benzenesulfonamide (119 mg, 0.38 mmol), cesium carbonate (244 mg, 0.75 mmol), and 3-(4-(bromomethyl)phenyl)-1,2,4-oxadiazole (99 mg, 0.41 mmol) according to the procedure described for 4-chloro-N-(4-cyanobenzyl)-N-(trans-2-(hydroxymethyl)cyclopentyl)benzenesulfonamide (Example 40) to give N-(4-(1,2,4-oxadiazol-3-yl)benzyl)-4-chloro-N-(cis-2-(hydroxymethyl)cycloheptyl)benzenesulfonamide (12 mg, 7%). $^1$H NMR (400 MHz, CDCl$_3$) δ ppm 8.75 (1H, s), 8.05 (2H, d, J=8.56 Hz), 7.68-7.70 (1H, m), 7.66-7.68 (1H, m), 7.47 (2H, d, J=8.56 Hz), 7.43-7.45 (1H, m), 7.41-7.43 (1H, m), 4.67 (1H, d, J=16.62 Hz), 4.44 (1H, d, J=16.62 Hz), 4.23-4.35 (1H, m), 3.60 (1H, dd, J=11.33, 8.56 Hz), 3.35 (1H, dd, J=11.46, 5.41 Hz), 1.99 (1H, br. s.), 1.38-1.81 (6H, m), 1.09-1.32 (5H, LC/MS R.T.=3.09 min; [M+H]$^+$=476.23.

Exemplification of Reaction Scheme 10

Example 47

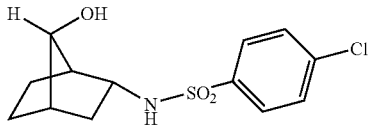

2-(4-Chlorophenylsulfonamido)bicyclo[2.2.1]heptan-7-ol

To a solution of 2-aminobicyclo[2.2.1]heptan-7-ol (prepared according to U.S. Pat. No. 5,583,221) (1.29 g, 10.1 mmol) and triethylamine (1.67 mL, 12 mmol) in 75 mL tetrahydrofuran was added 4-chlorobenzenesulfonyl chloride (2.53 g, 12 mmol). The reaction was stirred at room temperature for 2 h, then diluted into 150 mL ethyl acetate and washed with brine (100 mL). The organic layer was concentrated and purified by flash chromatography on a 40 g silica gel column using a gradient of 10 to 50% ethyl acetate in hexane over 25 min to give 2-(4-chlorophenylsulfonamido)bicyclo[2.2.1]heptan-7-ol (2.12 g, 70%). $^1$H NMR (400 MHz, CDCl$_3$) δ ppm 7.79-7.81 (1H, m), 7.77-7.79 (1H, m), 7.46-7.48 (1H, m), 7.44-7.46 (1H, m), 5.61 (1H, d, J=10.32 Hz), 4.00 (1H, s), 3.34-3.48 (1H, m), 2.00-2.04 (1H, m), 1.86 (1H, d, J=3.78 Hz), 1.83 (1H, br. s.), 1.68-1.76 (1H, m), 1.59-1.66 (1H, m), 1.37-1.54 (2H, m), 0.97-1.09 (2H, m). LC/MS R.T.=1.98 min; [M+H]$^+$=302.16.

Example 48

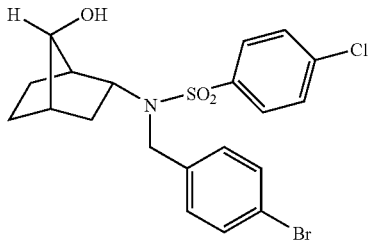

N-(4-Bromobenzyl)-N-(7-hydroxybicyclo[2.2.1]heptan-2-yl)-4-chlorobenzenesulfonamide
Compound 33

The title compound was synthesized from 2-(4-chlorophenylsulfonamido)bicyclo[2.2.1]heptan-7-ol (302 mg, 1.0 mmol), cesium carbonate (652 mg, 2.0 mmol), and 1-bromo-4-(bromomethyl)benzene (300 mg, 1.2 mmol) according to the procedure described for 4-chloro-N-(4-cyanobenzyl)-N-(trans-2-(hydroxymethyl)cyclopentyl)benzenesulfonamide (Example 2) to give N-(4-bromobenzyl)-N-(7-hydroxybicyclo[2.2.1]heptan-2-yl)-4-chlorobenzenesulfonamide (341 mg, 72%). $^1$H NMR (400 MHz, CDCl$_3$) δ ppm 7.65-7.72 (2H, m), 7.40-7.46 (2H, m), 7.37 (2H, d, J=8.56 Hz), 7.18 (2H, d, J=8.56 Hz), 4.68 (2H, dd, J=38.27, 17.12 Hz), 3.97 (1H, t, J=7.30 Hz), 3.77 (1H, s), 1.94 (1H, hr. s.), 1.79-1.88 (3H, m), 1.36-1.62 (3H, m), 1.00-1.12 (2H, m). LC/MS R.T.=2.33 min; [M+H]$^+$=470.03. HRMS [M+H]$^+$ calc'd 470.0192, found 470.0202.

Example 49

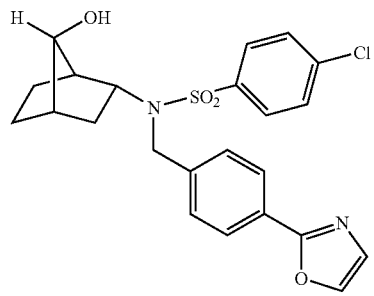

N-(4-(Oxazol-2-yl)benzyl)-N-(7-hydroxybicyclo[2.2.1]heptan-2-yl)-4-chlorobenzenesulfonamide
Compound 34

The title compound was synthesized from 2-(4-chlorophenylsulfonamido)bicyclo[2.2.1]heptan-7-ol (121 mg, 0.40 mmol), cesium carbonate (261 mg, 0.80 mmol), and 2-(4-(bromomethyl)phenyl)oxazole (114 mg, 0.48 mmol) according to the procedure described for 4-chloro-N-(4-cyanobenzyl)-N-(trans-2-(hydroxymethyl)cyclopentyl)benzenesulfonamide (Example 2) to give N-(4-bromobenzyl)-N-(7-hydroxybicyclo[2.2.1]heptan-2-yl)-4-N-(4-(oxazol-2-yl)benzyl)-N-(7-hydroxybicyclo[2.2.1]heptan-2-yl)-4-chlorobenzenesulfonamide (77 mg, 42%). $^1$H NMR (400 MHz, CDCl$_3$) δ ppm 7.93 (2H, d, J=8.31 Hz), 7.73 (2H, d, J=8.56 Hz), 7.67 (1H, s), 7.42 (4H, dd, J=13.47, 8.44 Hz), 7.17 (1H, s), 4.82 (2H, dd, J=44.57, 17.37 Hz), 4.04 (1H, dd, J=8.56, 6.55 Hz), 3.81 (1H, s), 2.30 (1H, br. s.), 1.88 (3H, br. s.), 1.40-1.65 (3H, m), 1.03-1.15 (2H, m). LC/MS R.T.=2.17 min; [M+H]$^+$=459.11. HRMS [M+H]$^+$ calc'd 459.1145, found 459.1136.

Example 50

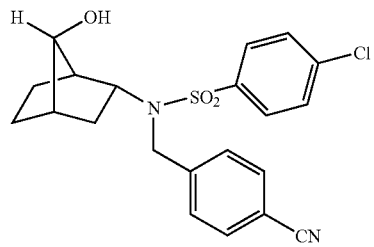

N-(4-Cyanobenzyl)-N-(7-hydroxybicyclo[2.2.1]heptan-2-yl)-4-chlorobenzenesulfonamide A solution of 2-(4-chlorophenylsulfonamido)bicyclo[2.2.1]heptan-7-ol (604 mg, 2.0 mmol), cesium carbonate (1.30 g, 4.0 mmol), and 4-(bromomethyl)benzonitrile (471 mg, 2.4 mmol) was stirred in 10 mL dimethylformamide for 1 h. The crude reaction product was treated with additional cesium carbonate (261 mg, 0.8 mmol) and 4-(bromomethyl)benzonitrile (94 mg, 0.5 mmol) to complete the reaction. The reaction was partitioned between 50 mL ethyl acetate and 50 mL 0.1 M HCl, concentrated and purified by flash chromatography on 120 g silica gel with 30 to 50% ethyl acetate in hexane to yield N-(4-cyanobenzyl)-N-(7-hydroxybicyclo

[2.2.1]heptan-2-yl)-4-chlorobenzenesulfonamide (412 mg, 49%). ¹H NMR (400 MHz, CDCl₃) δ ppm 7.70-7.77 (2H, m), 7.59 (2H, d, J=8.56 Hz), 7.44-7.50 (4H, m), 4.81 (2H, dd, J=39.53, 17.88 Hz), 4.06 (1H, t, J=7.81 Hz), 3.84 (1H, br. s.), 1.91 (1H, br. s.), 1.75-1.82 (2 Hon), 1.43-1.66 (3H, m), 1.07-1.17 (2H, m). LC/MS R.T.=1.97 min; [M+H]⁺=417.15.

Example 51

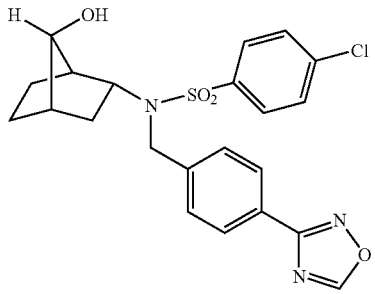

N-(4-(1,2,4-Oxadiazol-3-yl)benzyl)-N-(7-hydroxybicyclo[2.2.1]heptan-2-yl)-4-chlorobenzenesulfonamide Compound 35

A mixture of N-(4-cyanobenzyl)-N-(7-hydroxybicyclo[2.2.1]heptan-2-yl)-4-chlorobenzenesulfonamide (380 mg, 0.91 mmol) and hydroxylamine (500 up was refluxed in 20 mL ethanol for 2 h. The reaction was concentrated and dried under high vacuum. A portion of the crude amide oxime (25 mg) which was obtained was refluxed in triethylorthoformate (2 mL) for 5 h. The reaction was diluted into 20 mL ethyl acetate, washed with brine, and purified by flash chromatography on 4 g silica gel with 0 to 30% ethyl acetate in hexane to yield N-(4-(1,2,4-oxadiazol-3-yl)benzyl)-N-(7-hydroxybicyclo[2.2.1]heptan-2-yl)-4-chlorobenzenesulfonamide (11 mg, 44%). ¹H NMR (400 MHz, CDCl₃) δ ppm 8.73 (1H, s), 8.00-8.08 (2H, m), 7.68-7.79 (2H, m), 7.40-7.49 (4H, m), 4.83 (2H, q, J=17.54 Hz), 4.02-4.11 (1H, m), 3.83 (1H, s), 1.88 (1H, br. s.), 1.58-1.68 (2H, m), 1.43-1.55 (3H, m), 1.06-1.16 (2H, m). LC/MS R.T.=2.35 min; [M+H]⁺=460.13.

Exemplification of Reaction Scheme 11

Example 52

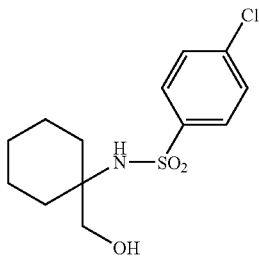

4-Chloro-N-(1-(hydroxymethyl)cyclohexyl)benzenesulfonamide

4-Chlorobenzenesulfonyl chloride (6.92 g, 32.8 mmol) was added to a solution of (1-aminocyclohexyl)methanol (prepared according to *Helv. Chirp. Acta,* 87:90-105 (2004)) (3.53 g, 27.3 mmol) and triethylamine (4.6 mL, 32.8 mmol) in 100 mL tetrahydrofuran at room temperature. The reaction was stirred overnight and concentrated. The residue was taken up in a mixture of 100 mL ethyl acetate and 100 mL brine. The organic layer was separated, dried over sodium sulfate, and purified by flash chromatography on 120 g silica gel with 20 to 100% ethyl acetate in hexane to yield 4-chloro-N-(1-(hydroxymethyl)cyclohexyl)benzenesulfonamide (6.07 g, 73%). ¹H NMR (400 MHz, CDCl₃) δ ppm 7.85-7.86 (1H, m), 7.81-7.84 (1H, m), 7.47-7.49 (1H, m), 7.44-7.46 (1H, m), 4.61 (1H, s), 3.60 (2H, d, J=5.54 Hz), 2.25 (1H, t, J=5.92 Hz), 1.57-1.69 (2H, m), 1.22-1.45 (8H, m). LC/MS R.T.=2.39 min; [M+H]⁺=304.03; [M+Na]⁺=326.05; [M-H]⁻=301.98.

Example 53

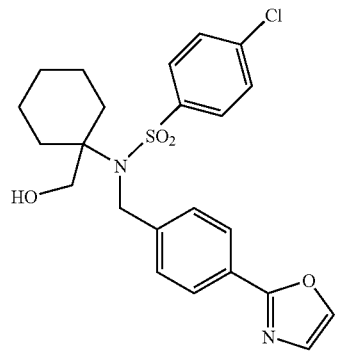

4-Chloro-N-(1-(hydroxymethyl)cyclohexyl)-N-(4-(oxazol-2-yl)benzyl)benzenesulfonamide Compound 36

The title compound was synthesized from 4-chloro-N-(1-(hydroxymethyl)cyclohexyl)benzenesulfonamide (114 mg, 0.38 mmol), cesium carbonate (244 mg, 0.75 mmol), and 2-(4-(bromomethyl)phenyl)oxazole (98 mg, 0.41 mmol) according to the procedure described for N-(4-bromobenzyl)-4-chloro-N-(1-(hydroxymethyl)cyclohexyl)benzenesulfonamide (Example 39) to give 4-chloro-N-(1-(hydroxymethyl)cyclohexyl)-N-(4-(oxazol-2-yl)benzyl)benzenesulfonamide (145 mg, 84%). ¹H NMR (400 MHz, CDCl₃) δ ppm 7.99 (2H, d, J=8.06 Hz), 7.77 (2H, d, J=8.56 Hz), 7.69 (1H, s), 7.45 (4H, dd, J=15.36, 8.56 Hz), 7.21 (1H, s), 4.78 (2H, s), 3.86 (2H, br. s.), 2.92 (1H, hr. s.), 1.81-1.90 (2H, m), 1.42-1.54 (5H, m), 1.20-1.31 (2H, m), 0.95-1.07 (1H, m). LC/MS R.T.=2.18 min; [M+H]⁺=461.08. HRMS [M+H]⁺ calc'd 461.1302, found 461.1321.

Example 54

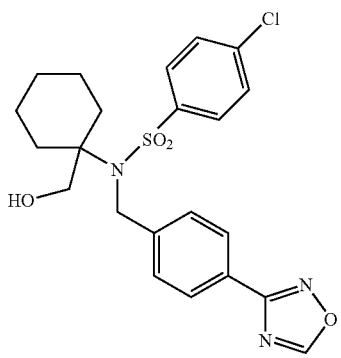

N-(4-(1,2,4-Oxadiazol-3-yl)benzyl)-4-chloro-N-(1-(hydroxymethyl)cyclohexyl)benzenesulfonamide Compound 37

The title compound was synthesized from 4-chloro-N-(1-(hydroxymethyl)cyclohexyl)benzenesulfonamide (114 mg, 0.38 mmol), cesium carbonate (244 mg, 0.75 mmol), and 3-(4-(bromomethyl)phenyl)-1,2,4-oxadiazole (99 mg, 0.41 mmol) according to the procedure described for N-(4-bromobenzyl)-4-chloro-N-(1-(hydroxymethyl)cyclohexyl)benzenesulfonamide (Example 39) to give N-(4-(1,2,4-oxadiazol-3-yl)benzyl)-4-chloro-N-(1-(hydroxymethyl)cyclohexyl)benzenesulfonamide (16 mg, 9%). $^1$H NMR (400 MHz, CDCl$_3$) δ ppm 8.75 (1H, s), 8.08 (2H, d, J=8.31 Hz), 7.80 (2H, d, J=8.56 Hz), 7.39-7.45 (4H, m), 4.38 (2H, d, J=5.79 Hz), 4.08-4.12 (2H, m), 1.68-1.82 (2H, m), 1.29-1.49 (8H, m). LC/MS R.T.=2.93 min; [M+Na]$^+$=484.20.

Biological Testing Methods

In Vitro Assays to Identify γ-Secretase Inhibitor Based on the Inhibition of Aβ Formation in Cultured Cells Cultured human cell lines, such as HEK293 and H4 cells, which express APP and γ-secretase activity or transfected derivative cell lines that overexpress wild-type APP, mutant APP, or APP fusion proteins will secrete Aβ peptides into the culture media that can be quantified as previously outlined (Dovey, H. et al., *J. Neurochem.*, 76:173-181 (2001)). The incubation of these cultured cells with γ-secretase inhibitors decreases the production of Aβ peptides. For instance, H4 cells stably transfected to overexpress the HPLAP-APP fusion protein described above were grown as above, detached, and adjusted to 2×10$^5$ cells/ml. 100 μl of the resulting suspension was then added to each well of a 96-well plate. After 4 hrs, the media was removed and replaced with 100 μl serum-free media containing various dilutions of the test compound. Plates were then incubated for 18 hrs at 37° C. and a 100 μl aliquot of the tissue culture supernatant was removed for determination of Aβ levels using time-resolved fluorescence of the homogenous sample as outlined above. Alternately, the other methods described above for Aβ determination could be used. The extent of Aβ inhibition was used to calculate the IC$_{50}$ value for the test compound. Compounds of the present invention are considered active when tested in the above assay if the IC$_{50}$ value for the test compound is less than 50 μM.

Examples of the results obtained when the invention compounds are subjected to the above described assay are shown in Table 1. In the table, an inhibitory concentration (IC$_{50}$) of less than or equal to 50 nM is represented by +++; between 50 nM and 500 nM by ++; between 500 nM and 5000 nM by +.

TABLE 1

| Examples of activity in the in vitro assay based on the inhibition of Aβ formation in cultured cells | |
|---|---|
| Compound No. | Activity (nM) |
| 1 | ++ |
| 2 | ++ |
| 3 | 223.30 |
| 4 | ++ |
| 5 | +++ |
| 6 | +++ |
| 7 | +++ |
| 8 | +++ |
| 9 | +++ |
| 10 | +++ |
| 11 | 0.32 |
| 12 | +++ |

TABLE 1-continued

| Examples of activity in the in vitro assay based on the inhibition of Aβ formation in cultured cells | |
|---|---|
| Compound No. | Activity (nM) |
| 13 | +++ |
| 14 | + |
| 15 | + |
| 16 | +++ |
| 17 | +++ |
| 18 | +++ |
| 19 | +++ |
| 20 | +++ |
| 21 | 0.15 |
| 22 | +++ |
| 23 | + |
| 24 | 2296.00 |
| 25 | +++ |
| 26 | +++ |
| 27 | +++ |
| 28 | +++ |
| 29 | +++ |
| 30 | +++ |
| 31 | ++ |
| 32 | +++ |
| 33 | + |
| 34 | + |
| 35 | 3238.00 |
| 36 | 345.80 |
| 37 | + |

The disclosure provided above is given by way of illustration and is not to be construed as limiting the invention to the specific aspects disclosed. It is intended that variations of the invention are possible within the spirit of the invention. For example, in addition to the compounds of the invention described herein, the invention also encompasses enantiomers and diastereomers thereof.

What is claimed is:

1. A compound of formula I:

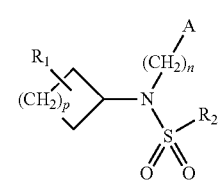

wherein:

A is

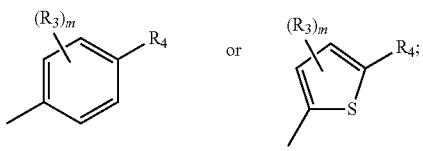

$R_1$ is —CH$_2$F, CH$_2$OH, —CH(CH$_3$)OH, —C(CH$_3$)$_2$OH, —COCH$_3$, or $R_1$ is —CHOH wherein, when $R_1$ is CHOH, the carbon atom of $R_1$ is bonded to two different positions on the cyclic alkyl ring of Compound I to form a bridged ring system;

$R_2$ is selected from the group consisting of phenyl, thiophene and pyridine, each optionally substituted with 1, 2, 3, or 4 substituents selected from the group consisting of hydrogen, halogen and trifluoromethyl;

$R_3$, if present, is halogen;

$R_4$ is

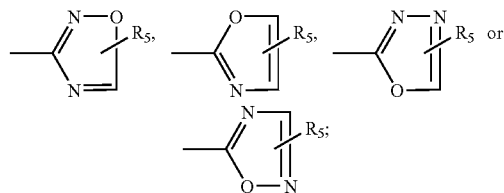

$R_5$ is H, or $C_{1-3}$alkyl $CF_3$;

m is 0, 1, 2, 3 or 4;

n is 0, 1, 2, 3, or 4;

p is 0, 1, 2, 3, 4 or 5;

or a pharmaceutically acceptable salt thereof.

2. The compound of claim 1 wherein A is

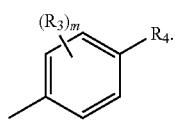

3. The compound of claim 1 wherein n is 0.

4. The compound of claim 1 wherein n is 1, 2, 3, or 4.

5. The compound of claim 1 wherein n is 1.

6. The compound of claim 1 wherein $R_4$ is

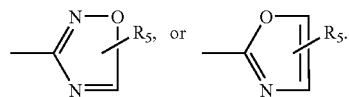

7. The compound of claim 1 wherein $R_5$ is H.

8. The compound of claim 1 wherein $R_5$ is $C_{1-3}$alkyl or $CF_3$.

9. The compound of claim 1 wherein $R_3$ is F, Cl or Br.

10. The compound of claim 9 wherein $R_3$ is F.

11. The compound of claim 1 wherein m is 0.

12. The compound of claim 1 wherein in is 1 or 2.

13. The compound of claim 1 wherein $R_2$ is selected from the group consisting of phenyl, thiophene and pyridine, each optionally substituted with one substituent selected from the group consisting of hydrogen, halogen and trifluoromethyl.

14. The compound of claim 1 wherein $R_2$ is selected from the group consisting of phenyl, thiophene and pyridine, each optionally substituted with 2, 3, or 4 substituents selected from the group consisting of hydrogen, halogen and trifluoromethyl.

15. The compound of claim 1 wherein $R_1$ is —$CH_2F$, —$CH_2OH$, —$CH(CH_3)OH$, —$C(CH_3)_2OH$, or —$COCH_3$.

16. The compound of claim 15 wherein $R_1$ is —$CH_2F$, —$CH_2OH$, —$CH(CH_3)OH$, —$C(CH_3)_2OH$.

17. The compound of claim 16 wherein $R_1$ is —$CH_2OH$.

18. The compound of claim 1 wherein p is 2, 3 or 4.

19. A compound of formula II:

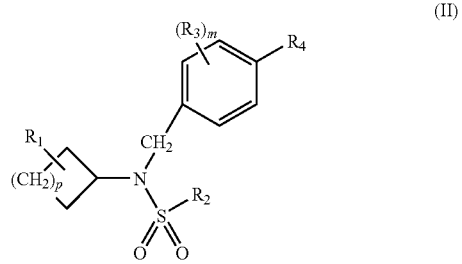

wherein:

$R_1$ is —$CH_2F$, $CH_2OH$, —$CH(CH_3)OH$, —$C(CH_3)_2OH$, —$COCH_3$, or $R_1$ is —CHOH wherein, when $R_1$ is CHOH, the carbon atom of $R_1$ is bonded to two different positions on the cyclic alkyl ring of Compound II to form a bridged ring system;

$R_2$ is

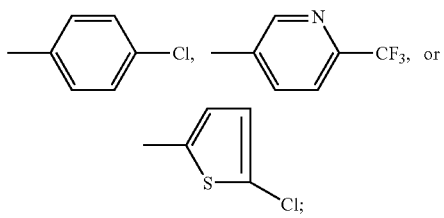

$R_3$, if present, is F;

$R_4$ is

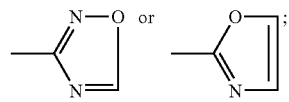

m is 0, 1 or 2;

p is 2, 3 or 4;

or a pharmaceutically acceptable salt thereof.

20. The compound of 19 wherein $R_2$ is

21. The compound of claim 19 wherein $R_1$ is —$CH_2F$, —$CH_2OH$, —$CH(CH_3)OH$, —$C(CH_3)_2OH$, or —$COCH_3$.

22. The compound of claim 21 wherein $R_1$ is —$CH_2OH$.

23. The compound of claim 19 wherein p is 3.

24. A compound of formula III:

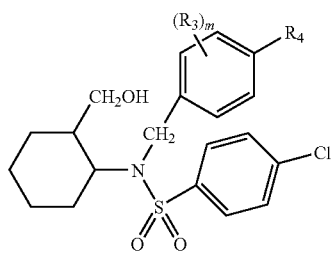

wherein:

R₃, if present, is F;

R₄ is

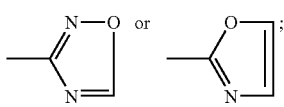

m is 0, 1 or 2;

or a pharmaceutically acceptable salt thereof.

25. The compound of claim 24 wherein R₃ is F.

26. The compound of claim 24 wherein m is 1 or 2.

27. A compound having the following structure:

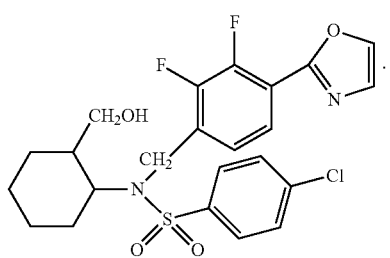

28. A compound having the following structure:

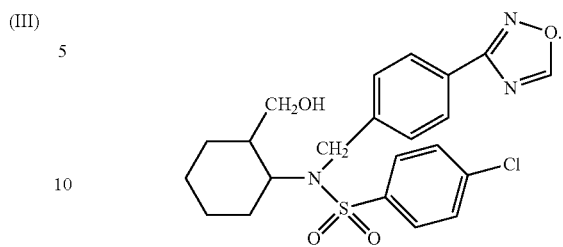

29. A compound having the following structure:

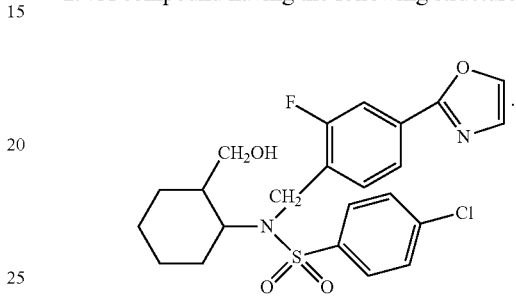

30. A compound having the following structure:

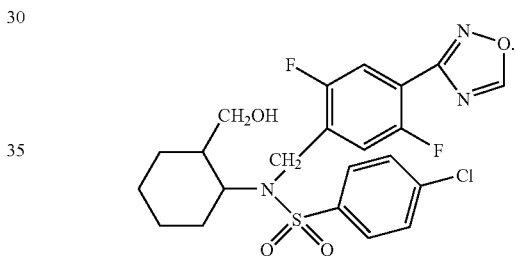

31. A composition comprising a compound of claim 1, or a pharmaceutically acceptable salt thereof, and a pharmaceutically acceptable carrier.

* * * * *